(12) United States Patent
Nobles et al.

(10) Patent No.: US 7,601,161 B1
(45) Date of Patent: Oct. 13, 2009

(54) SUTURING DEVICE

(75) Inventors: Anthony A. Nobles, Fountain Valley, CA (US); Rod Peterson, Anaheim, CA (US); Steven Decker, Anaheim, CA (US); Benjamin Brosh, Mission Viejo, CA (US)

(73) Assignee: Quick Pass, Inc., Fountain Valley, CA (US)

( * ) Notice: Subject to any disclaimer, the term of this patent is extended or adjusted under 35 U.S.C. 154(b) by 1295 days.

(21) Appl. No.: 09/607,845

(22) Filed: Jun. 30, 2000

Related U.S. Application Data

(60) Provisional application No. 60/142,106, filed on Jul. 2, 1999.

(51) Int. Cl.
*A61B 17/04* (2006.01)
*A61B 17/12* (2006.01)

(52) U.S. Cl. .................. 606/145; 606/139; 606/144
(58) Field of Classification Search ......... 606/144–148, 606/139, 222, 205, 207, 223–227
See application file for complete search history.

(56) References Cited

U.S. PATENT DOCUMENTS

| | | | |
|---|---|---|---|
| 1,989,919 A | 2/1935 | Everitt | |
| 2,637,290 A | 5/1953 | Sigoda | |
| 2,945,460 A | 7/1960 | Kagiyama | |
| 3,842,840 A | 10/1974 | Schweizer | |
| 4,107,953 A | 8/1978 | Casillo | |
| 4,417,532 A | 11/1983 | Yasukata | |
| 4,484,580 A | 11/1984 | Nomoto et al. | |
| 4,827,931 A | 5/1989 | Longmore | |
| 4,841,888 A | 6/1989 | Mills | |
| 5,224,948 A | 7/1993 | Abe et al. | |
| 5,281,237 A | 1/1994 | Gimpelson | |
| 5,391,174 A | 2/1995 | Weston | |
| 5,405,354 A | 4/1995 | Sarrett | |
| 5,417,699 A * | 5/1995 | Klein et al. | 606/144 |
| 5,431,666 A | 7/1995 | Sauer et al. | |
| 5,454,823 A | 10/1995 | Richardson et al. | |
| 5,458,609 A * | 10/1995 | Gordon et al. | 606/144 |

(Continued)

FOREIGN PATENT DOCUMENTS

WO    WO93/01750    2/1993

(Continued)

*Primary Examiner*—Eduardo C Robert
*Assistant Examiner*—Julianna N Harvey
(74) *Attorney, Agent, or Firm*—Knobbe, Martens, Olson & Bear, LLP

(57) ABSTRACT

A suturing device for suturing a portion of biological tissue includes a needle attached to a suture, a needle holder that releasably holds the needle, and a needle driver adapted to be advanced and retracted substantially parallel to a longitudinal axis of the suturing device. A distal needle holder adapted to releasably hold the needle is positioned in a distal position relative to the portion of biological tissue and a distal end of the needle driver is positioned in a proximal position relative to the portion of biological tissue. The needle is positioned in either the proximal position or the distal position. The needle driver is moved longitudinally in a first direction along a path substantially parallel to the longitudinal axis such that the needle and suture pass through the portion of biological tissue, thereby forming a suture incision through which the suture passes. By repeating the above-described processes, a series of stitches is thereby formed.

7 Claims, 25 Drawing Sheets

U.S. PATENT DOCUMENTS

| | | | |
|---|---|---|---|
| 5,520,702 A | 5/1996 | Sauer et al. | |
| 5,562,686 A | 10/1996 | Sauer et al. | |
| 5,571,090 A | 11/1996 | Sherts | |
| 5,632,751 A | 5/1997 | Piraka | |
| 5,643,289 A | 7/1997 | Sauer et al. | |
| 5,669,917 A | 9/1997 | Sauer et al. | |
| 5,707,379 A | 1/1998 | Fleenor et al. | |
| 5,709,693 A | 1/1998 | Taylor | |
| 5,746,753 A * | 5/1998 | Sullivan et al. | 606/147 |
| 5,759,188 A | 6/1998 | Yoon | |
| 5,766,183 A | 6/1998 | Sauer | |
| 5,843,100 A | 12/1998 | Meade | |
| 5,908,428 A * | 6/1999 | Scirica et al. | 606/139 |
| 6,332,889 B1 | 12/2001 | Sancoff et al. | |
| 6,383,208 B1 | 5/2002 | Sancoff et al. | |
| 6,527,785 B2 | 3/2003 | Sancoff et al. | |
| 6,663,643 B2 | 12/2003 | Field et al. | |
| 6,679,895 B1 | 1/2004 | Sancoff et al. | |
| 6,682,540 B1 | 1/2004 | Sancoff et al. | |
| 6,767,352 B2 | 7/2004 | Field et al. | |
| 6,786,913 B1 | 9/2004 | Sancoff | |

FOREIGN PATENT DOCUMENTS

| | | |
|---|---|---|
| WO | WO 95/25468 | 9/1995 |
| WO | WO 97/27807 | 8/1997 |

* cited by examiner

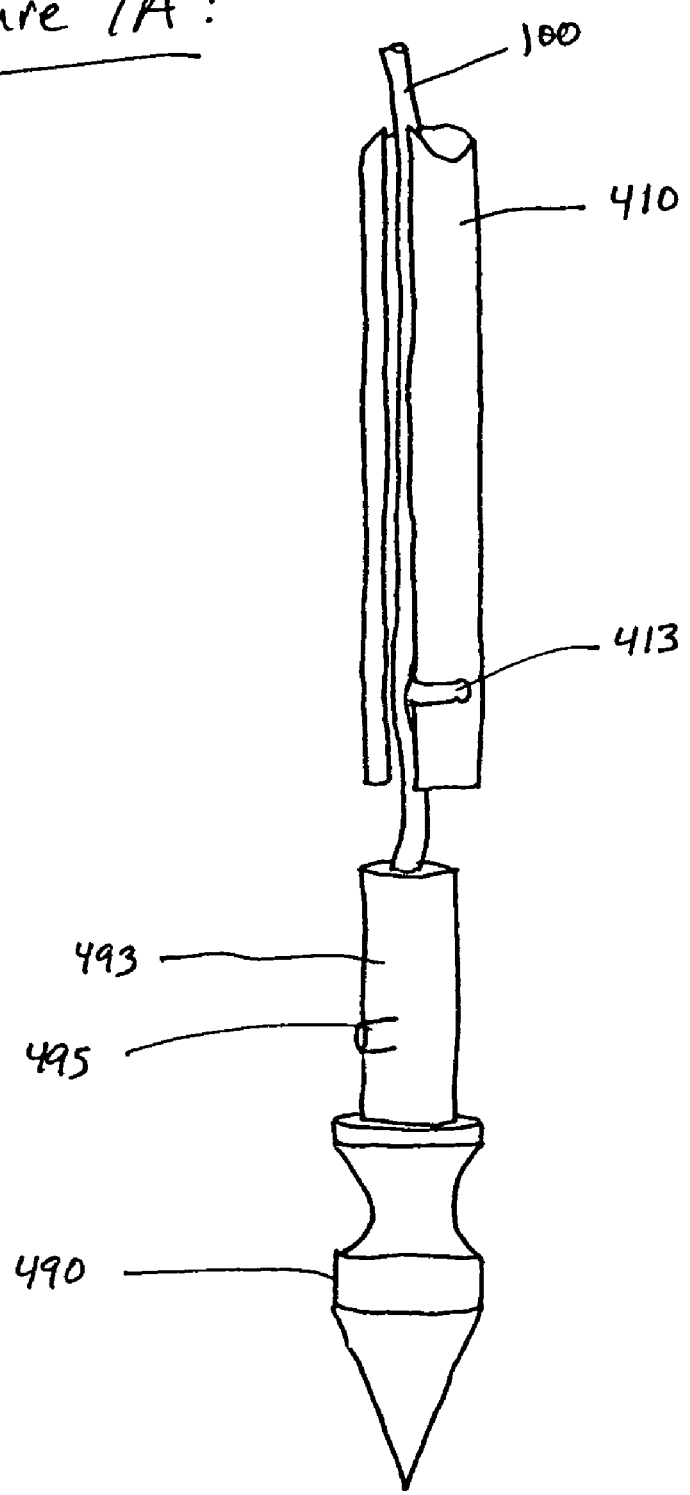

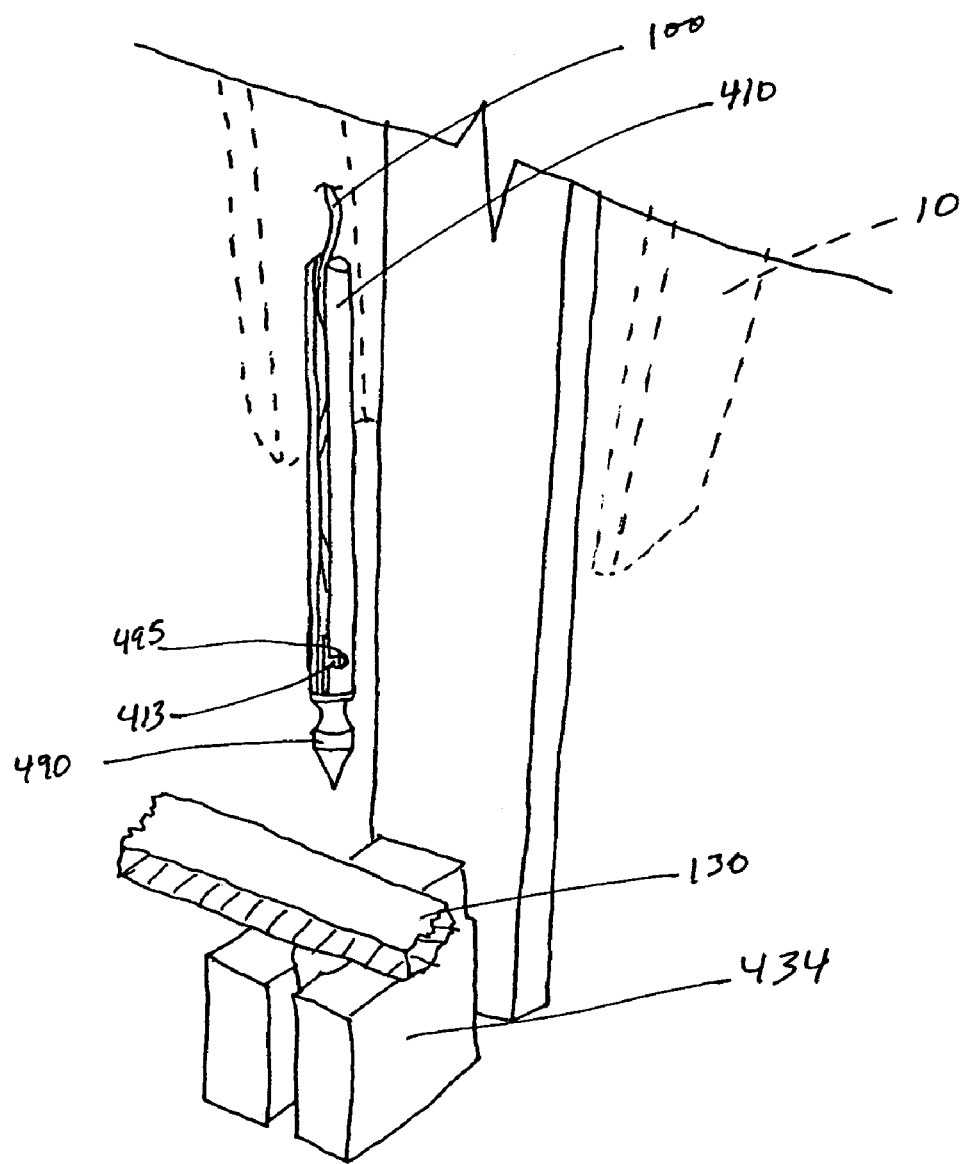

SUTURING DEVICE

This application claims priority to U.S. Provisional Patent Application No. 60/142,106, filed Jul. 2, 1999.

BACKGROUND OF THE INVENTION

1. Field of the Invention

The present invention relates generally to medical devices. Specifically, the present invention relates to devices for facilitating the suturing of biological tissue.

2. Description of the Related Art

Sutures are frequently used to close various openings such as cuts, punctures, and incisions in various places in the human body. Because of their importance and frequent use, several types of sutures and devices for their implantation and extraction have been developed. Typically, suturing is performed by repeatedly passing a sharp suture needle attached to a length of suture material through portions of tissue to be sutured together, thereby forming loops of suture material passing through the tissue. The free ends of the suture material are then tied together to complete the suturing procedure.

There are however some circumstances under which it is not feasible to use conventional sutures and suturing methods to close an opening. It is often difficult to reach some suture sites with existing suturing devices because of the depth of the suture site within the human anatomy, the size of the suture site, and/or the restriction of surrounding organs and tissue. For example, where the tissue to be sutured is within the patient's thorax (such as for an end-to-side anastomosis in a cardiac bypass procedure), traditional methods of suturing are invasive and time consuming.

SUMMARY OF THE INVENTION

The present invention provides a device and method for suturing a portion of biological tissue.

One aspect of the present invention is a method of suturing a portion of biological tissue using a suturing device having a longitudinal axis, a needle attached to a suture, a needle driver, and at least one needle holder. A distal needle holder adapted to releasably hold the needle is positioned in a distal position relative to the portion of biological tissue and a distal end of the needle driver is positioned in a proximal position relative to the portion of biological tissue. The needle is positioned in either the proximal position or the distal position. The needle driver is moved longitudinally in a first direction along a path substantially parallel to the longitudinal axis such that the needle and suture pass through the portion of biological tissue, thereby forming a suture incision through which the suture passes. The above-described processes are repeated to form a series of stitches.

Another aspect of the present invention is a method of suturing a portion of biological tissue. A needle is releasably held by a first needle holder, the needle being attached to a suture. The first needle holder is placed in a proximal position relative to a portion of biological tissue and a second needle holder is placed in a distal position relative to the portion of biological tissue, so that the portion of biological tissue is between the first needle holder and the second needle holder. A force is applied to the needle by engaging the needle with a needle driver and extending the needle driver in the distal direction. This extension of the needle driver transfers the needle from the first needle holder, through the portion of biological tissue between the first and second needle holders, to the second needle holder. The needle driver is disengaged from the needle and retracted in the proximal direction away from the needle and the first and second needle holders. The first and second needle holders are laterally withdrawn from the portion of biological tissue, and the positions of the first and second needle holders are exchanged, so that the first needle holder is in a distal position relative to the second needle holder and the needle.

Another aspect of the resent invention is a suturing device for suturing a portion of biological tissue. The suturing device comprises a needle attached to a suture, a needle holder that releasably holds the needle, and a needle driver adapted to be advanced and retracted substantially parallel to a longitudinal axis of the suturing device.

Another aspect of the present invention is a suturing device for suturing a portion of biological tissue. The suturing device comprises a needle attached to a suture, and a first needle holder adapted to releasably hold the needle. The first needle holder is alternately positionable in a proximal position or a distal position relative to the portion of biological tissue. The suturing device further comprises a second needle holder adapted to releasably hold the needle. The second needle holder is coupled to the first needle holder to be positionable in the proximal position when the first needle holder is in the distal position, and in the distal position when the first needle holder is in the proximal position. The suturing device further comprises a needle driver that transfers the needle from the needle holder in the proximal position, through the portion of biological tissue between the first and second needle holders, to the needle holder in the distal position.

Another aspect of the present invention is a suturing device for suturing a portion of biological tissue. The suturing device comprises a needle attached to a suture, and a needle holder adapted to releasably hold the needle. The needle holder is positioned distally relative to the portion of biological tissue. The suturing device further comprises a needle driver adapted to releasably hold the needle and to advance the needle along a path substantially parallel to the longitudinal axis of the suturing device.

BRIEF DESCRIPTION OF THE DRAWINGS

FIG. 7A is a perspective view of an alternative embodiment of the present invention comprising a needle which is lockable to a needle driver.

FIG. 7B is a perspective view of the needle and needle driver of the alternative embodiment of FIG. 7A.

DETAILED DESCRIPTION OF THE PREFERRED EMBODIMENT

Figure 1:
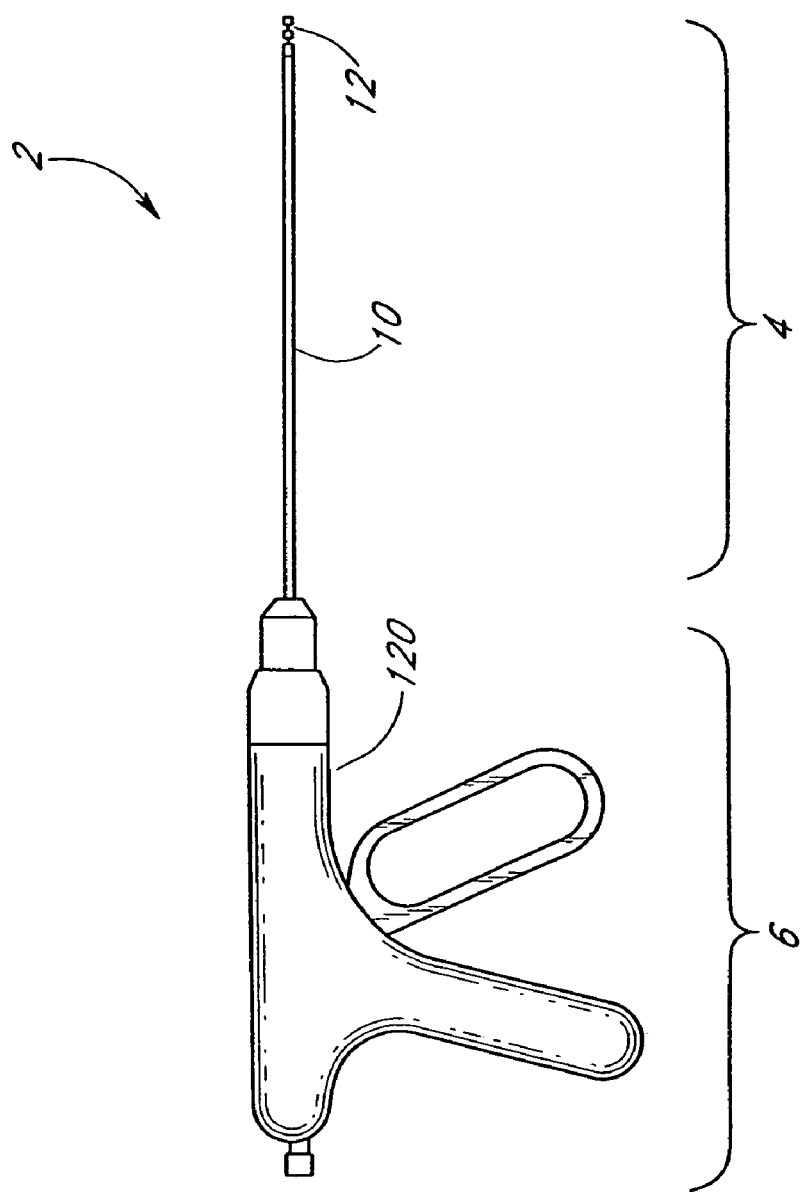
FIG. 1 illustrates a suturing device compatible with the preferred embodiment of the present invention, the suturing device comprising a proximal portion including a handle, and a distal portion including an elongated body and a suturing mechanism assembly.

FIG. 1 illustrates a preferred embodiment of a suturing device 2 which allows a physician to suture biological tissue at a variety of locations and at a variety of depths within a body. For example, the suturing device 2 may be used to suture two layers or sections of tissue, such as an end-to-side anastomosis.

The suturing device 2 of the preferred embodiment illustrated in FIG. 1 comprises a distal portion 4 and a proximal portion 6, each extending along a common longitudinal axis. The distal portion 4 of the suturing device 2 is the portion farthest from the physician or user (i.e., closest to the suture site). The proximal portion 6 of the suturing device 2 is the portion closest to the user. In the description below, the distal direction is defined as the direction along the longitudinal axis away from the user, and the proximal direction is defined as the direction along the longitudinal axis toward the user.

Figure 2:
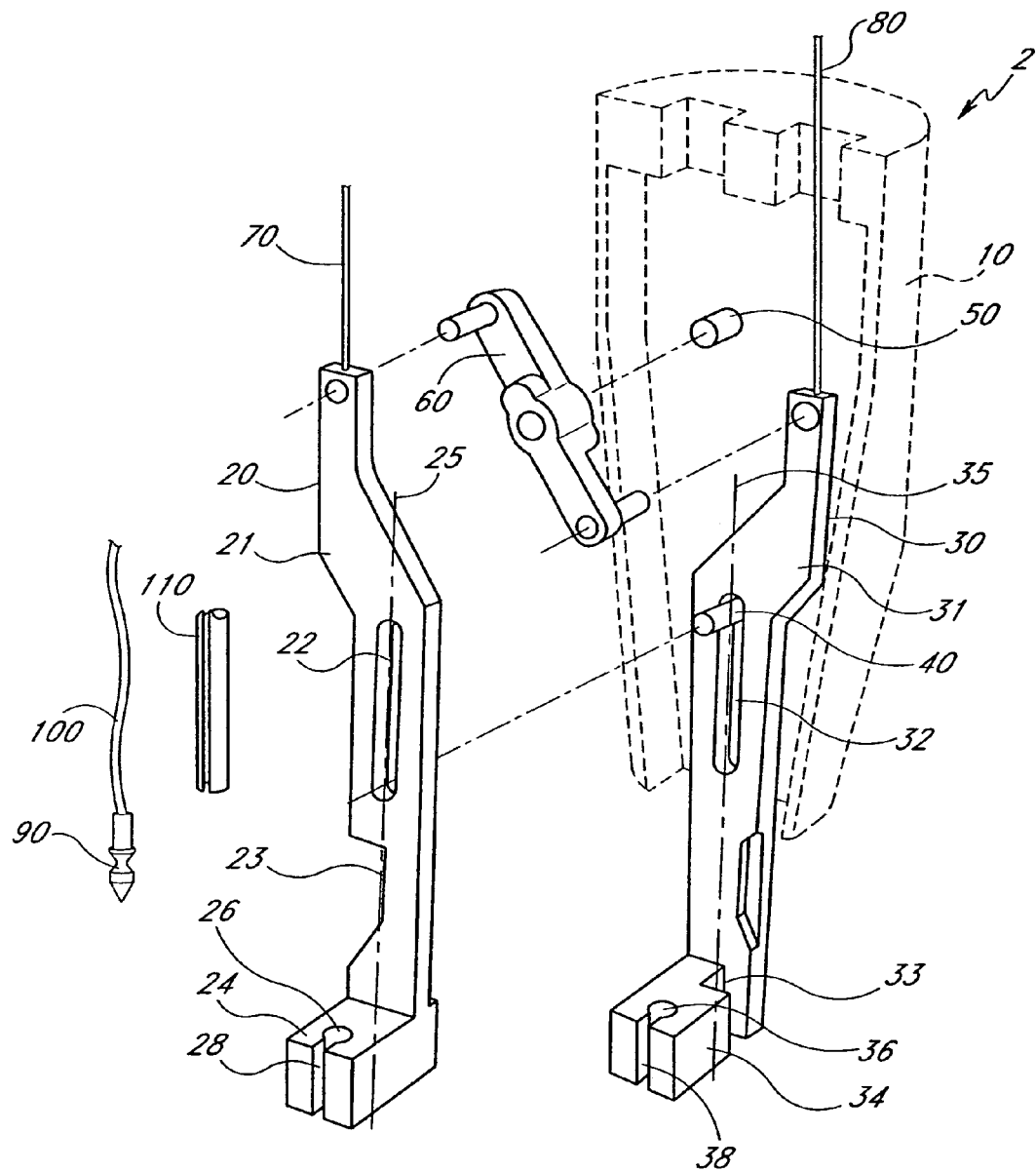
FIG. 2 is an exploded view of a suturing mechanism assembly compatible with the preferred embodiment of the present invention.

The distal portion 4 of the suturing device 2 comprises an elongated body 10, and a suturing mechanism assembly 12. As illustrated in FIG. 2, the suturing mechanism assembly 12 comprises a first arm 20, a second arm 30, a guide pin 40, a pivot pin 50, a cross piece 60, a first arm actuator rod 70, a second arm actuator rod 80, a needle 90, a suture 100, and a needle driver 110. The proximal portion 6 of the suturing device 2 comprises a handle 120, which is illustrated in more detail in FIGS. 5A-5D.

The elongated body 10 extends along the longitudinal axis from the handle 120 to the suturing mechanism assembly 12 positioned near the distal end of the distal portion 4 of the suturing device 2. To provide a clear view of the suturing mechanism assembly 12 in FIGS. 2-5F, the elongated body 10 is shown with a cover portion removed, the cover portion including a guide hole for the suture 100 and the needle driver 110. The elongated body 10 is rotatable about the longitudinal axis with respect to the handle 120, thereby enabling the suturing mechanism assembly 12 to be rotationally manipulated with respect to the handle 120 to position the suturing mechanism assembly 12 without rotating the handle 120. Alternatively, only a distal portion of the elongated body 10 and the suturing mechanism assembly 12 are rotatable about the longitudinal axis with respect to the handle 120. In certain embodiments, the elongated body 10 is flexible thereby enabling the suturing device 2 to be inserted along a curving puncture wound or body lumen.

Referring to FIG. 2, the first arm 20 comprises a first arm body 21, a first guide slot 22, a first notch 23, and a first needle holder 24 near the distal end of the first arm 20 with a first needle groove 26 and a first suture release opening 28. Similarly, the second arm 30 comprises a second arm body 31, a second guide slot 32, a second notch 33, and a second needle holder 34 near the distal end of the second arm 30 with a second needle groove 36 and a second suture release opening 38. The first arm body 21 and the second arm body 31 are generally bar-shaped, each with a long axis 25, 35 and a rectangular cross-section. In the preferred embodiment illustrated in FIG. 2, each arm body 21, 31 has a corresponding guide slot 22, 32 which is straight and substantially parallel to the long axis 25, 35 of the arm body 21, 31. In other embodiments, the guide slots 22, 32 are curved, or include angles defined by multiple straight sections. Both the first arm body 21 and second arm body 31 are rotatably coupled near their proximal ends to opposite ends of the cross piece 60, which is rotatably coupled near its center to the pivot pin 50. Both the guide pin 40 and the pivot pin 50 are fixedly connected to the elongated body 10. The first arm body 21 and second arm body 31 are also both slidably coupled to the guide pin 40 via the first guide slot 22 and the second guide slot 32, respectively.

Figure 3A:
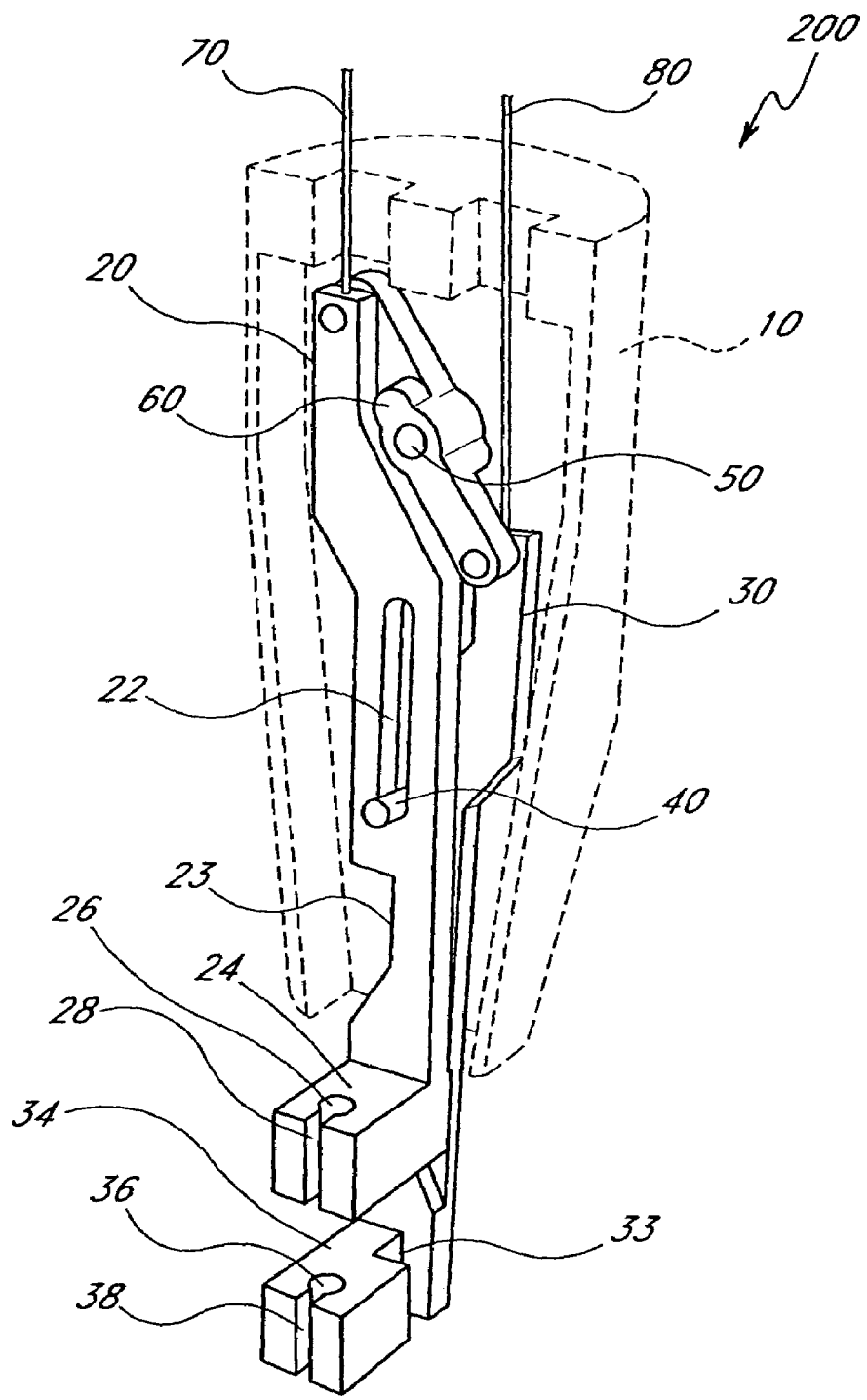
FIG. 3A is a perspective view of the suturing mechanism assembly of FIG. 1 in the first orientation.
Figure 3B:
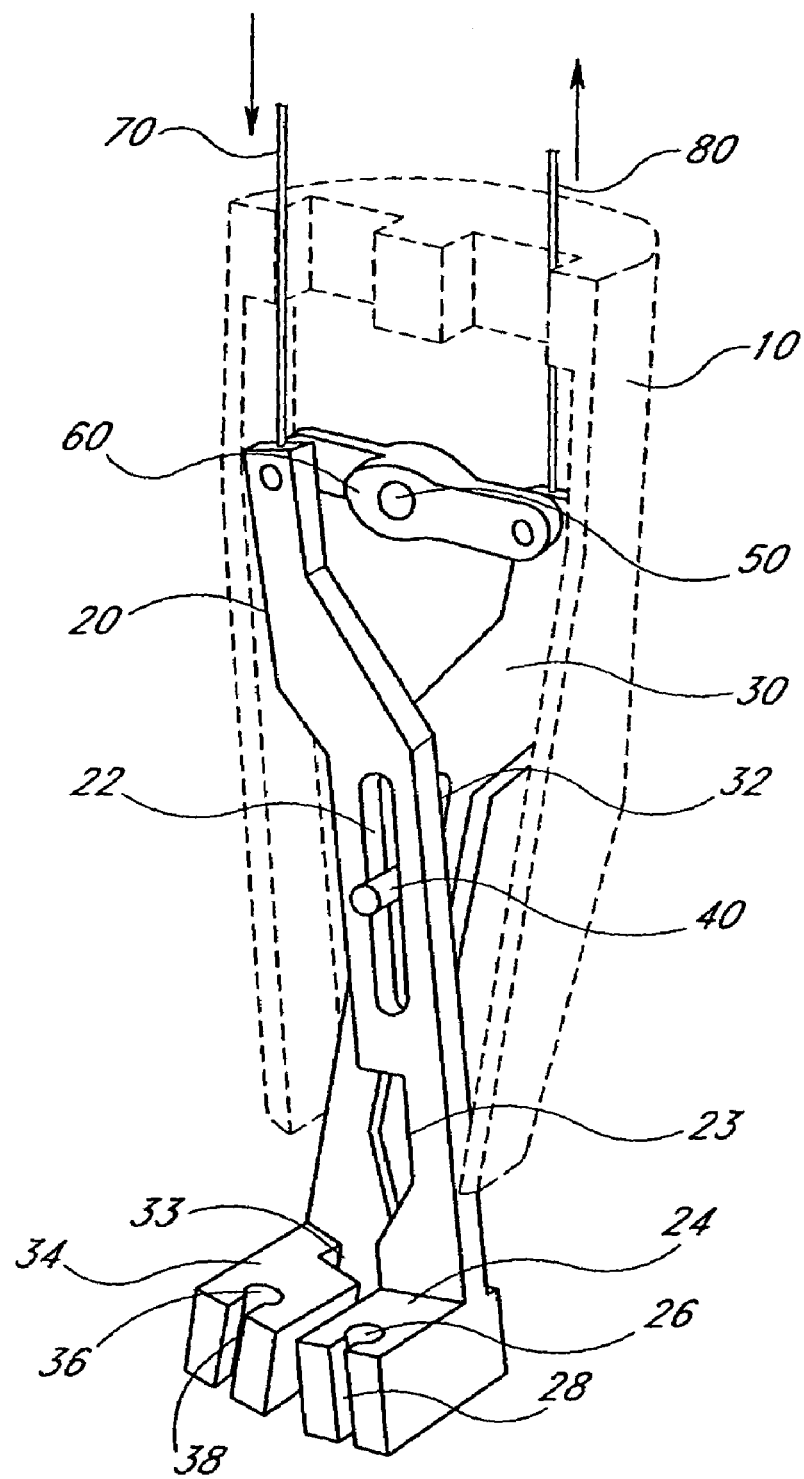
FIG. 3B is a perspective view of the suturing mechanism assembly of FIG. 1 in an intermediate orientation between the first orientation and the second orientation.
Figure 3C:
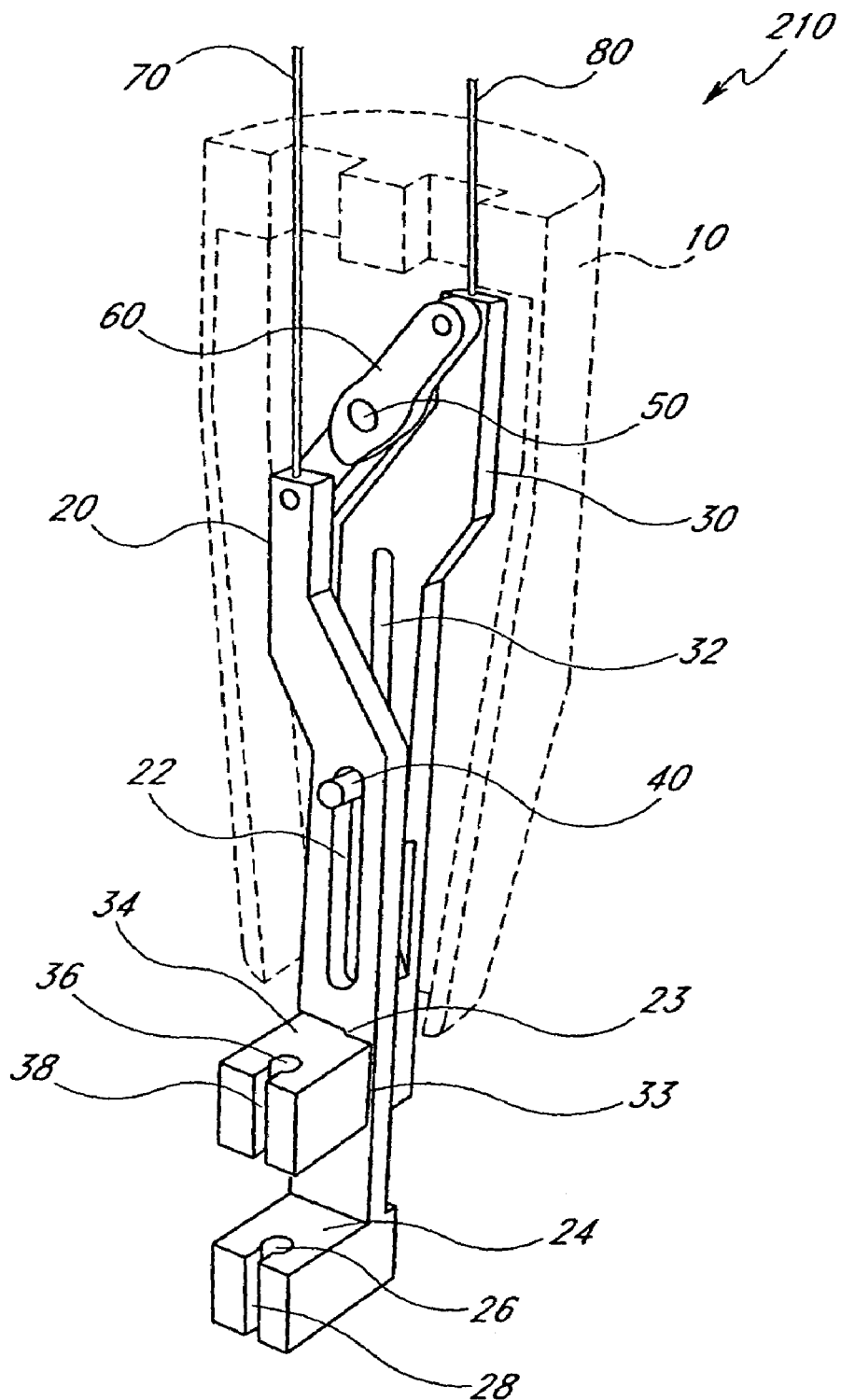
FIG. 3C is a perspective view of the suturing mechanism assembly of FIG. 1 in the second orientation.

The first arm actuator rod 70 is coupled to the first arm 20 near the end at which the first arm 20 is coupled to the cross piece 60, and the second arm actuator rod 80 is coupled to the second arm 30 near the end at which the second arm 30 is coupled to the cross piece 60. Both the arm actuator rods 70, 80 extend from the suturing mechanism assembly 12 to the handle 120, and are movable longitudinally along the elongated body 10. As illustrated in FIGS. 3A-3C, the first arm 20 and second arm 30 are movable relative to one another to a first orientation 200, a second orientation 210, and a plurality of intermediate orientations between the first orientation 200 and second orientation 210. With the suturing device 2 in the first orientation 200, pushing the first arm actuator rod 70 longitudinally in the distal direction and pulling the second arm actuator rod 80 longitudinally in the proximal direction rotates the cross piece 60 counter-clockwise about the pivot pin 50, until the second orientation 210 is reached. Conversely, with the suturing device 2 in the second orientation 210, pulling the first arm actuator rod 70 longitudinally in the proximal direction and pushing the second arm actuator rod 80 longitudinally in the distal direction rotates the cross piece 60 clockwise about the pivot pin 50, until the first orientation 200 is reached. In other embodiments, the rotation of the cross piece 60 is achieved by using only one actuator rod which is pushed and pulled accordingly to alternate between the first orientation 200 and the second orientation 210.

In the first orientation 200 illustrated in FIG. 3A, the long axes 25, 35 of the first arm body 21 and second arm body 31 are substantially parallel to one another, and the first needle groove 26 is substantially colinear to the second needle groove 36. In addition, the distal end of the first guide slot 22 is in proximity to the guide pin 40, and the proximal end of the second guide slot 32 is in proximity to the guide pin 40. The first needle holder 24 is in a proximal position relative to the second needle holder 34 (i.e., the first needle holder 24 is closer to the handle 120 than is the second needle holder 34).

FIG. 3B illustrates an intermediate position of the first and second arms 20, 30 of the preferred embodiment of the present invention. By rotating the cross piece 60 counter-clockwise about the pivot pin 50, both the first arm 20 and second arm 30 are translated and rotated relative to the guide pin 40. As the cross piece 60 is rotated counter-clockwise, the first needle holder 24 is translated in the distal direction and the second needle holder 34 is translated in the proximal direction. In addition, by virtue of the rotation of the first and second arms 20, 30 about the guide pin 40, the first and second needle holders 24, 34 avoid contact with one another.

In FIG. 3C, the cross piece 60 is rotated further in the counter-clockwise direction about the pivot pin 50, until the second orientation 210 is reached. In the second orientation 210, the first needle holder 24 is in a distal position relative to the second needle holder 34. Furthermore, the long axes 25, 35 of the first arm body 21 and second arm body 31 are again substantially parallel to one another, and the first needle groove 26 is again substantially colinear to the second needle groove 36. This colinearity of the first and second needle grooves 26, 36 is due in part to the interlocking of the first notch 23 and the second notch 33, to avoid the first arm body 21 from interfering with the second needle holder 34.

The first and second needle grooves 26, 36 of the preferred embodiment illustrated in FIGS. 3A-3C are configured to be substantially colinear with each other and parallel with the longitudinal axis of the elongated body 10 when the suturing device 2 is in either the first orientation 200 or the second orientation 210. Alternatively, in other embodiments, the first and second needle grooves 26, 36 can be configured to be substantially colinear with each other, but at an angle with respect to the longitudinal axis of the elongated body 10. In still other embodiments of the present invention, the first and second needle grooves 26, 36 may be curved to form sections of a semi-circle or arc, such as to accommodate a curved needle 90 and a curved needle driver 110.

Figure 4:
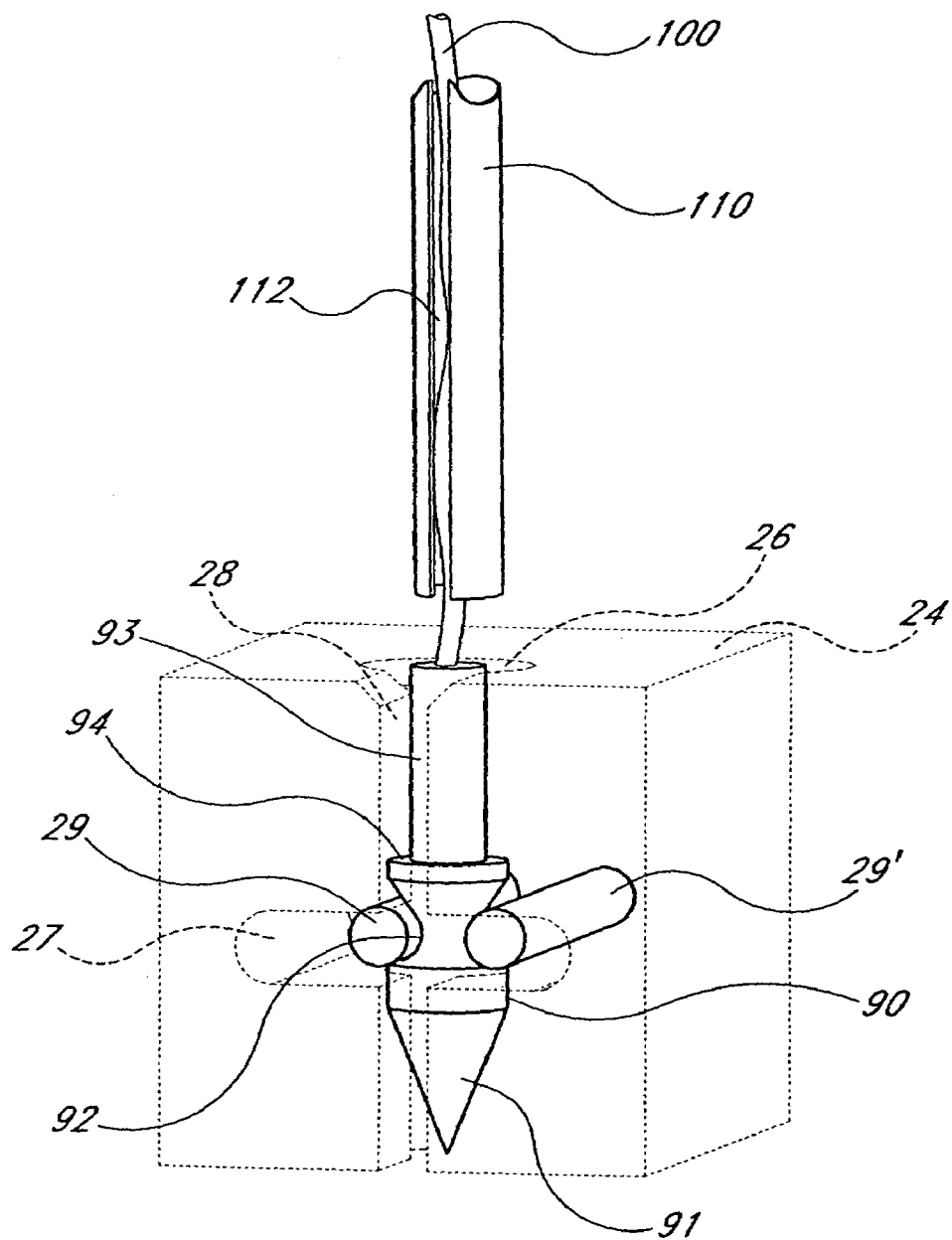
FIG. 4 is a perspective view of a needle, needle holder, and needle driver compatible with the preferred embodiment of the present invention.

FIG. 4 illustrates the first needle holder 24, needle 90, suture 100, and needle driver 110 of the preferred embodiment of the present invention. In the preferred embodiment, the second needle holder 34 is substantially identical to the first needle holder 24. The needle holders 24, 34 are generally block-shaped, although in other embodiments, the needle holders 24, 34 can be spherical, cylindrical, or any other suitable configuration. As illustrated in FIG. 4, the first needle holder 24 has a first needle groove 26 and a first suture release opening 28. The first needle groove 26 extends from the proximal surface to the distal surface of the first needle holder 24, and it has a substantially circular cross-section. The first suture release opening 28 also extends from the proximal surface to the distal surface of the first needle holder 24, and is cut into the opposite surface of the first needle holder 24 from the first arm body 21. The first suture release opening 28 is sufficiently wide to allow the suture 100 to be pulled laterally out of the first needle holder 24. In addition, the first needle holder 24 has a first spring slot 27 cut substantially perpendicularly to the first needle groove 26. The first spring slot 27 contains a pair of first spring pins 29, 29' which each have one end fixedly connected to the first needle holder 24, the other end free to move within the first spring slot 27. Each of the first spring pins 29, 29' intersects the opposite sides of the first needle groove 26. When the free ends of the first spring pins 29, 29' are deflected outward away from the first needle groove 26, each first spring pin 29, 29' generates a restoring force in the inward direction toward the first needle groove 26. The second needle holder 34 similarly includes a second needle groove 36, a second suture release opening 38, a second spring slot 37 and a pair of second spring pins 39, 39', all configured similarly to their counterparts in the first needle holder 24.

The needle 90, which is substantially cylindrically symmetric, has a pointed distal end 91, a relief 92, a generally cylindrical proximal end 93, and an upper surface 94 as illustrated in FIG. 4. The pointed distal end 91 is configured to enable the needle 90 to be pushed along a distal direction piercing biological tissue. The relief 92 is configured to engage the spring pins 29, 29', 39, 39' so that the needle 90 is securely held in the needle holders 24, 34, but can be pushed out the distal end of the needle grooves 26, 36 when sufficient force is applied to the needle 90 in the distal direction. In the preferred embodiment, the suture 100 is fixedly attached near the proximal end 93 of the needle 90. However, in other embodiments, the suture 100 can be fixedly attached to other portions of the needle 90.

The needle driver 110 is a hollow cylinder with an inner diameter which is larger than the outer diameter of the suture 100 and the outer diameter of the proximal end 93 of the needle 90. The suture 100 extends along a length of the needle driver 110 through the center of the needle driver 110. The needle driver 110 is colinear with the first needle groove 26 and the second needle groove 36, and is sufficiently rigid to apply a force to the needle 90 in the distal direction sufficient to pass the needle 90 and the suture 100 through a portion of biological tissue between the needle holders 24, 34. For example, the needle driver 110 is capable of applying to the needle 90 a force sufficient to disengage the needle 90 from the first spring pins 29, 29', push the needle 90 out the distal end of the first needle groove 26, through a portion of biological tissue between the first needle holder 24 and second needle holder 34, into the proximal end of the second needle groove 36 of the second needle holder 34, where the needle is engaged by the second spring pins 39, 39'. The needle driver 110 also has a suture release slit 112 which extends from the distal end of the needle driver 110 along at least a portion of the needle driver 110 in the proximal direction. The suture release slit 112 is sufficiently wide to allow the suture 100 to be pulled out of the needle driver 100.

FIGS. 5A-5F illustrate one preferred embodiment of the present invention during the suturing of a portion of biological tissue 130. A physician or medical practitioner first inserts the suturing device 2 through a wound, such as an incision in a patient's muscle tissue, skin tissue, organ, blood vessel, etc. The physician then positions the suturing mechanism assembly 12 to suture a portion of biological tissue 130.

Figure 5A:
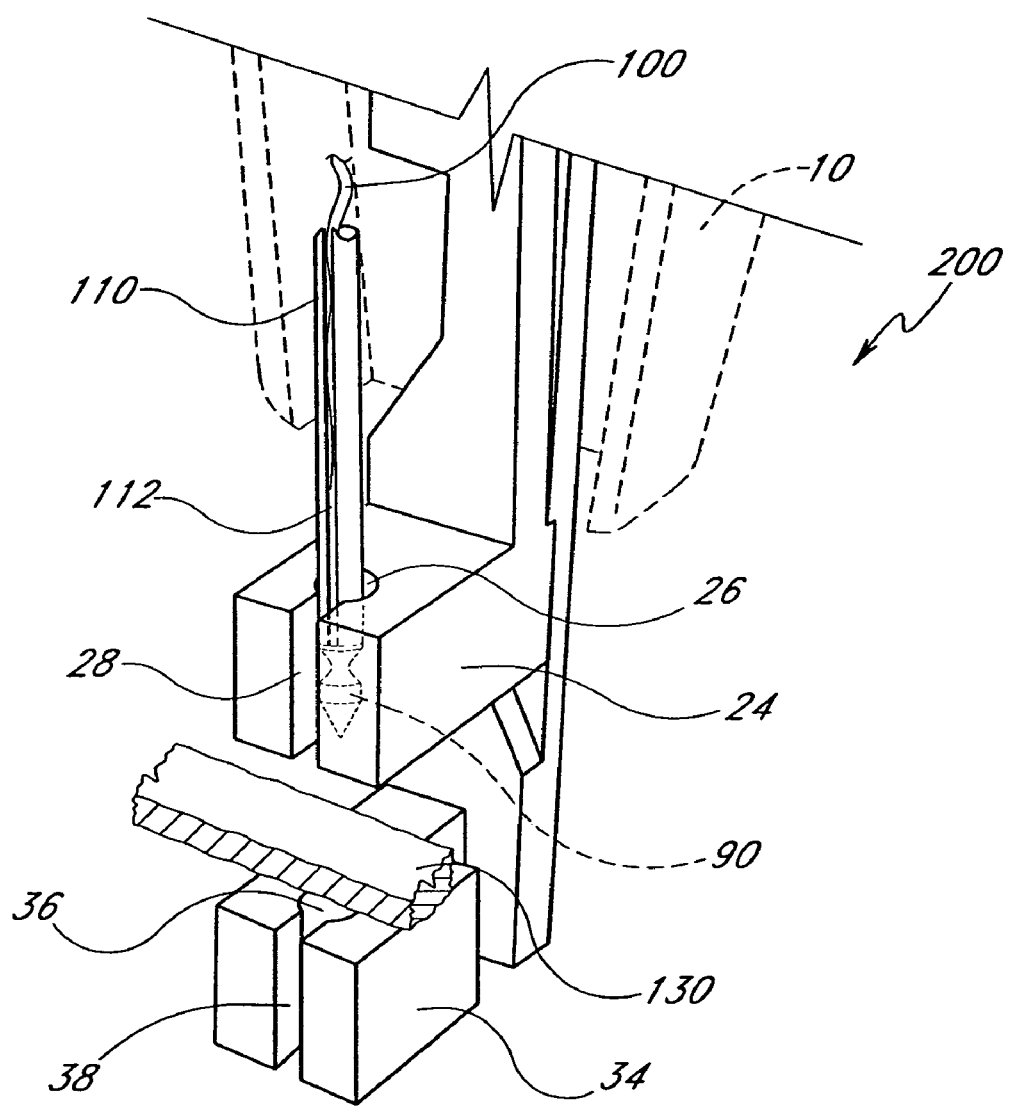
FIG. 5A is a perspective view of the preferred embodiment of the present invention in the first orientation immediately prior to the creation of a first stitch of the suture through a portion of biological tissue.

FIG. 5A illustrates the configuration immediately prior to the creation of a first stitch of the suture 100 through a portion of biological tissue 130. The suturing mechanism assembly 12 is in the first orientation 200 with the first needle holder 24 in a proximal position relative to the tissue 130, and the second needle holder 34 in a distal position relative to the tissue 130. The needle 90 is held in the first needle groove 26 of the first needle holder 24 by the first spring pins 29, 29' (not shown). The needle driver 110 is positioned so that its distal end is engaged with the proximal end 93 and upper surface 94 of the needle 90, and the suture 100 extends from the proximal end 93 of the needle 90 through a length of the needle driver 110.

Figure 5B:
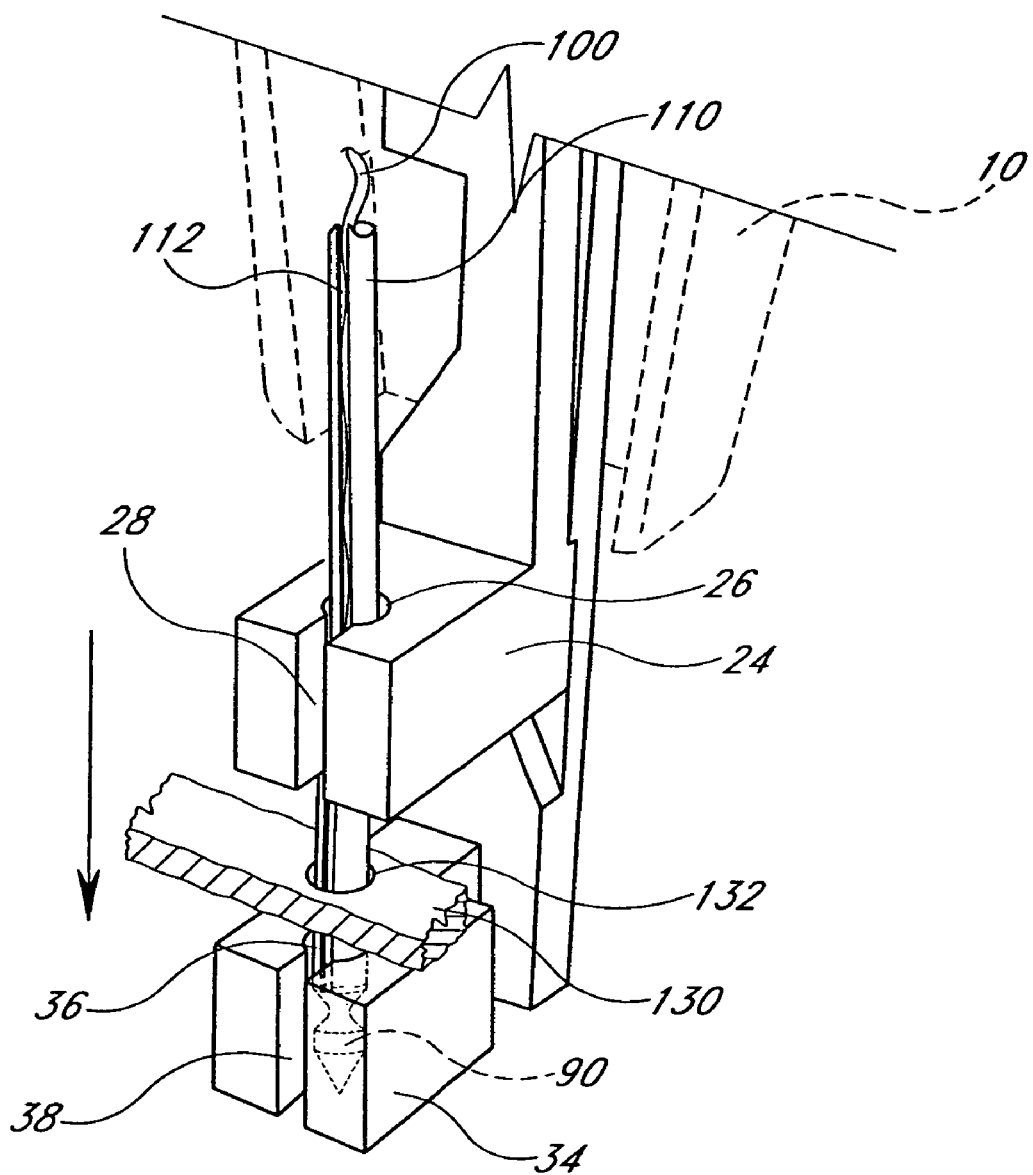
FIG. 5B is a perspective view of the preferred embodiment of the present invention after the needle driver pushes the needle and suture in the distal direction substantially parallel to the longitudinal axis, thereby piercing a portion of biological tissue.

The needle driver 110 is then extended distally, thereby applying a force to the needle 90 and moving it distally towards the second needle holder 34 in the longitudinal direction. The needle 90 is thus pushed distally away from the first spring pins 29, 29', out the distal end of the first needle groove 26 of the first needle holder 24, piercing the tissue 130, and into the proximal end of the second needle groove 36 of the second needle holder 34, where it is secured by the second spring pins 39, 39' (not shown). As shown in FIG. 5B, after such driving of the needle 90, the suture 100 and the needle driver 110 extend from the needle 90 in the second needle groove 36 of the second needle holder 34, through the tissue 130, and through the first needle groove 26 of the first needle holder 24, thereby forming a first suture incision 132.

Figure 5C:
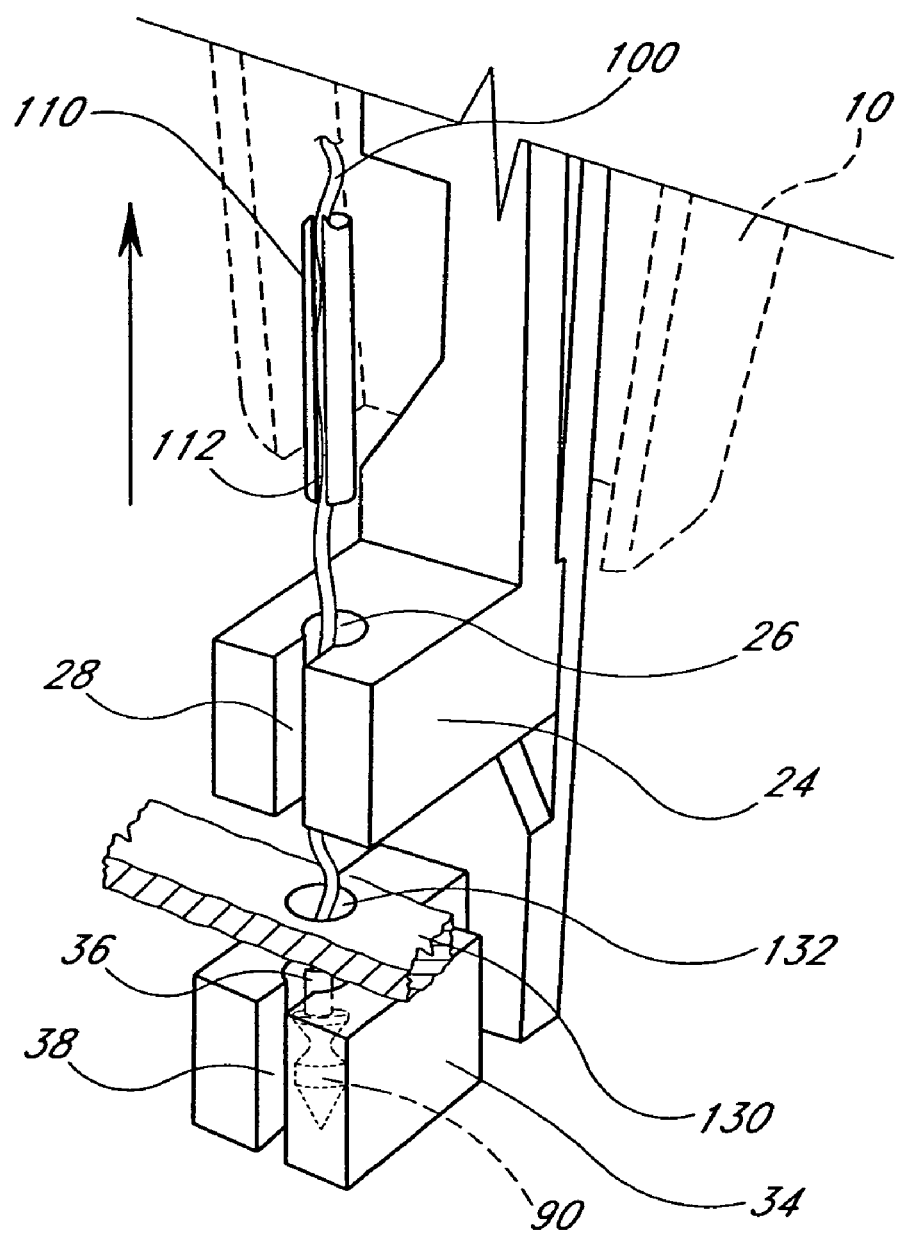
FIG. 5C is a perspective view of the preferred embodiment of the present invention after retracting the needle driver from the tissue.

The needle driver 110 is then retracted in the proximal direction away from the needle 90 held in the second needle holder 34. As shown in FIG. 5C, once retracted, the needle driver 110 no longer passes through the first needle holder 24, the tissue 130, or the second needle holder 34. However, the suture 100 remains attached to the proximal end 93 of the needle 90, passing from the second needle holder 34, through the tissue 130, and through the first needle groove 26 of the first needle holder 24.

Figure 5D:
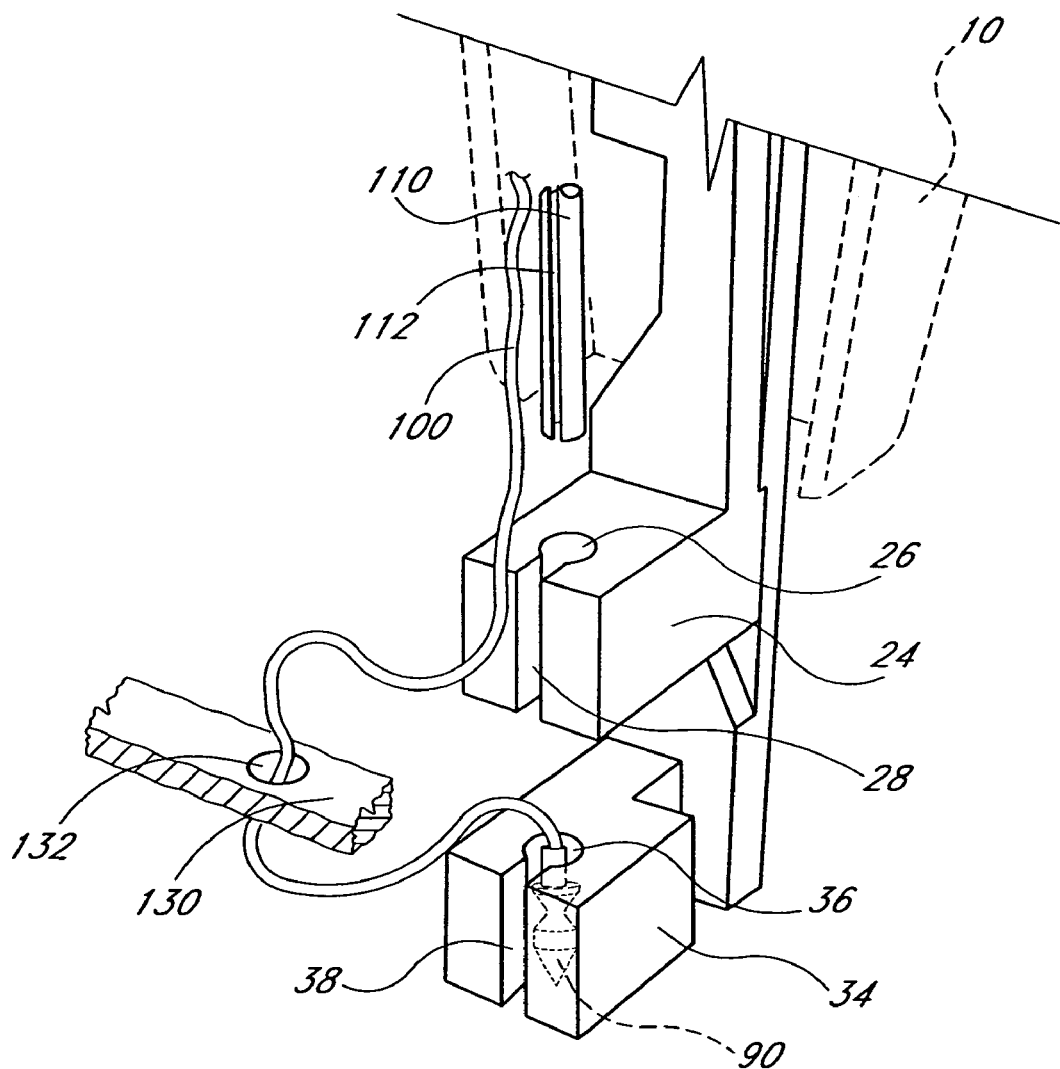
FIG. 5D is a perspective view of the preferred embodiment of the present invention after withdrawing the suturing device away from the tissue.

The suturing mechanism assembly 12 is then withdrawn from the first suture incision 132 where the suture 100 passes through the tissue 130. As shown in FIG. 5D, withdrawal of the suturing mechanism assembly 12 from the tissue 130 pulls the suture 100 out of the first needle holder 24 through the first suture release opening 28 and out of the needle driver 110 through the suture release slit 112. Because the suture 100 is attached to the needle 90 held in the second needle holder 34, the withdrawal of the suturing mechanism assembly 12 from the tissue 130 also pulls an additional length of suture 100 out of the needle driver 110. This additional length of suture 100 provides sufficient slack in the suture 100 for the movement of the suturing mechanism assembly 12 from the first orientation 200 to the second orientation 210. The suturing mechanism assembly 12 is withdrawn from the tissue 130 a sufficient distance to permit unobstructed movement of the arms 20, 30 between the first orientation 200 and the second orientation 210.

Figure 5E:
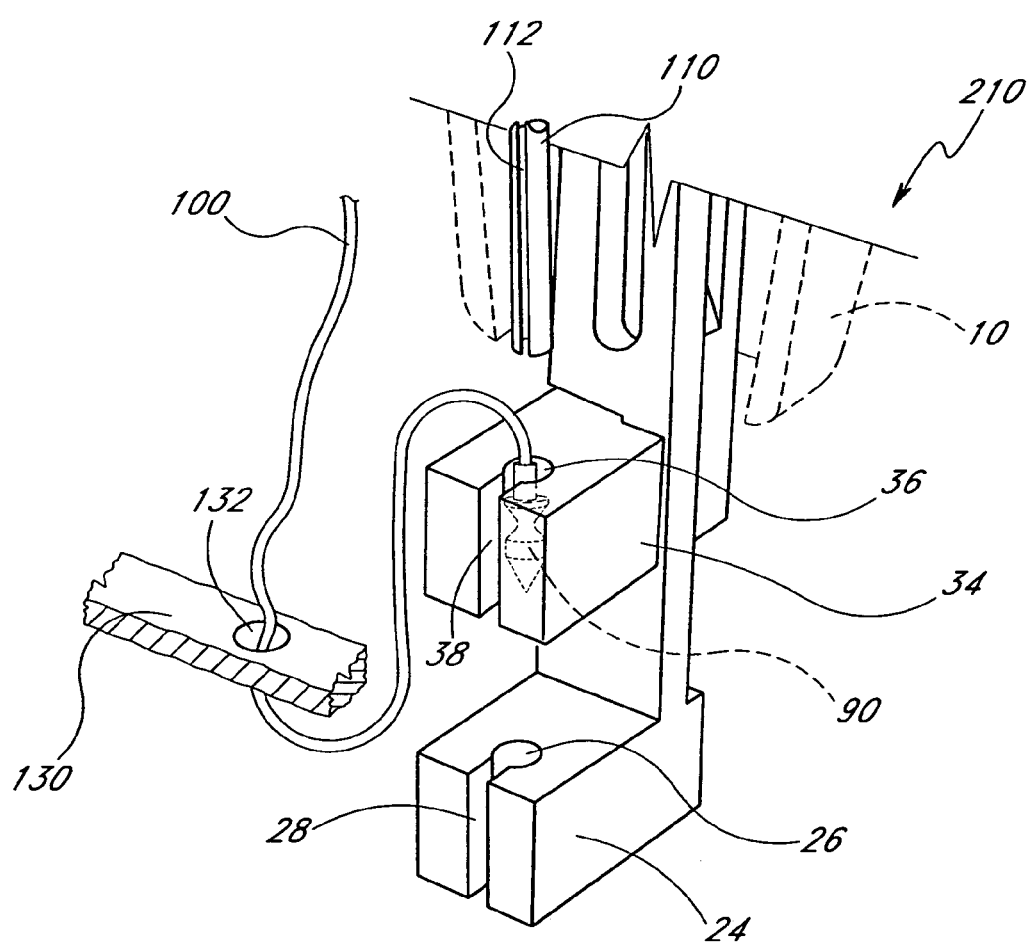
FIG. 5E is a perspective view of the preferred embodiment of the present invention in the second orientation after creating a first stitch in the first orientation.
Figure 5F:
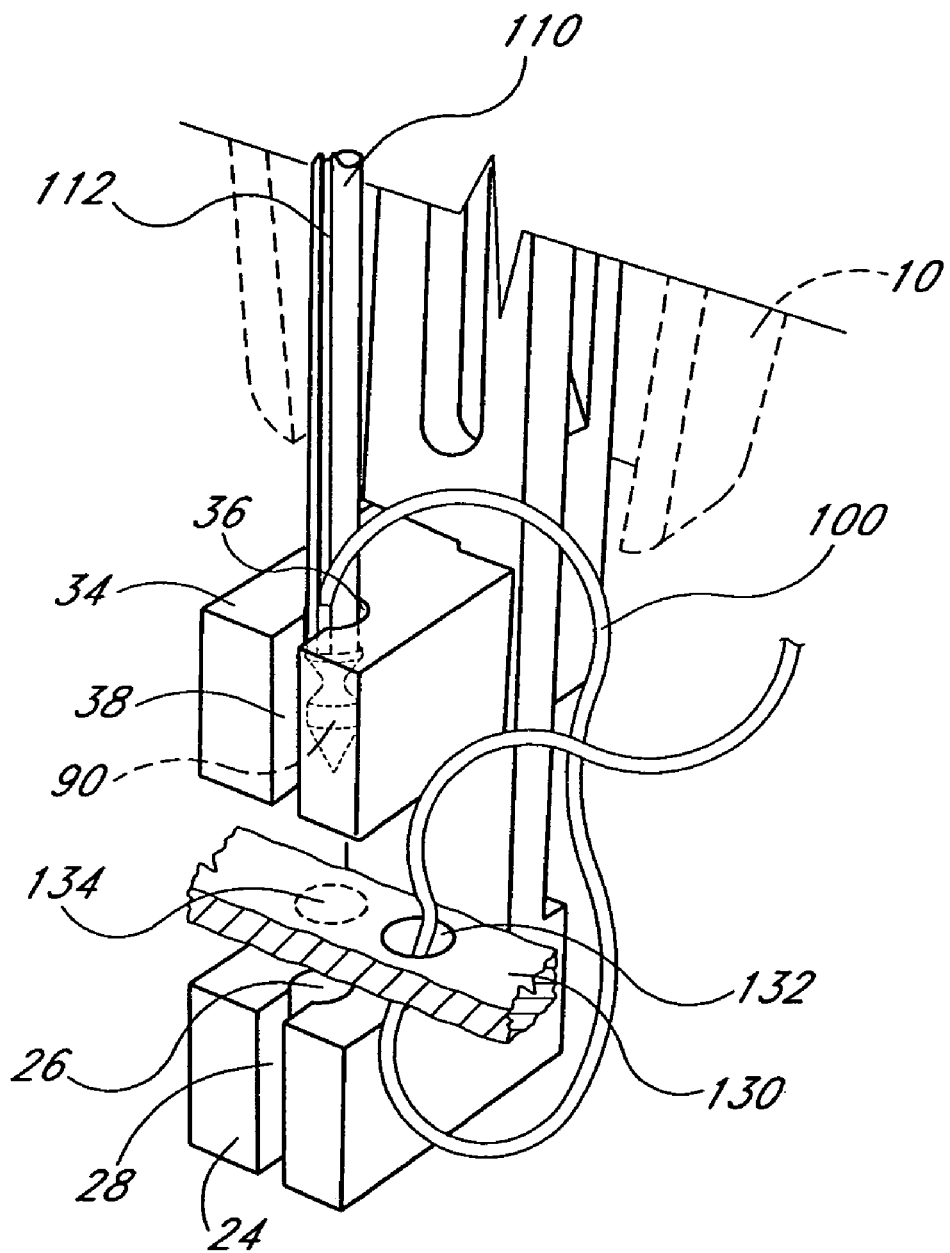
FIG. 5F is a perspective view of the preferred embodiment of the present invention in the second orientation immediately prior to the creation of a second stitch of the suture through a portion of biological tissue.
Figure 6A:
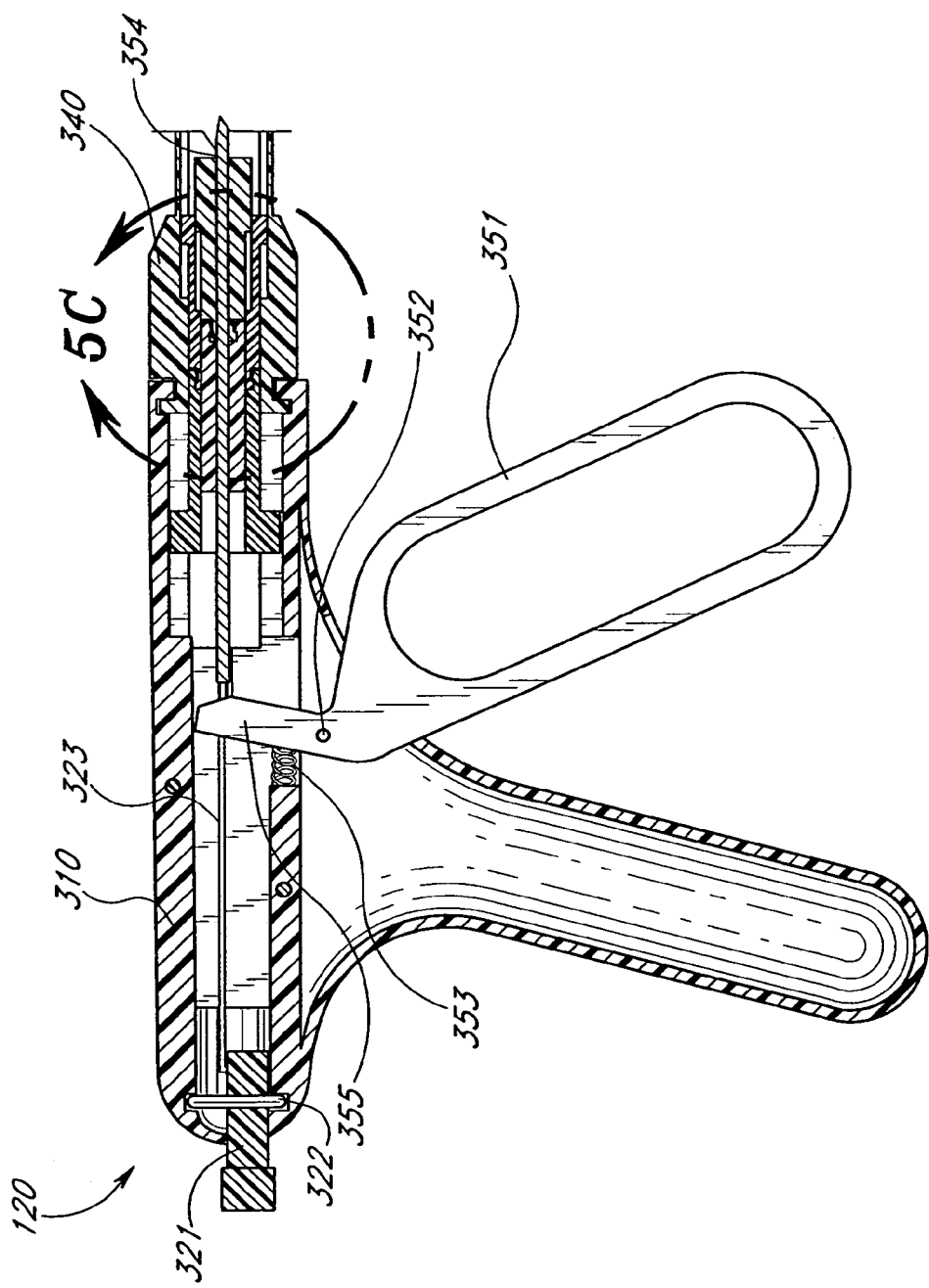
FIG. 6A is a cross-sectional side view of the preferred embodiment of a handle compatible with the present invention.
Figure 6B:
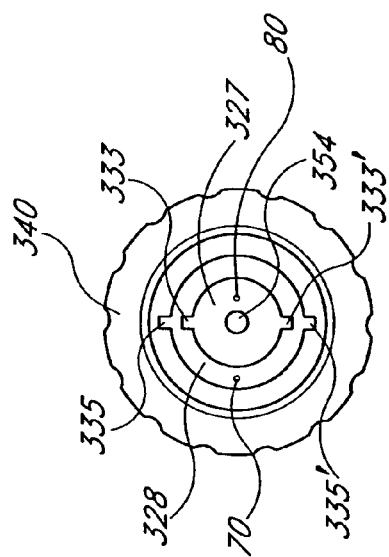
FIG. 6B is a view along the longitudinal axis in the proximal direction of the preferred embodiment of a handle compatible with the present invention.
Figure 6C:
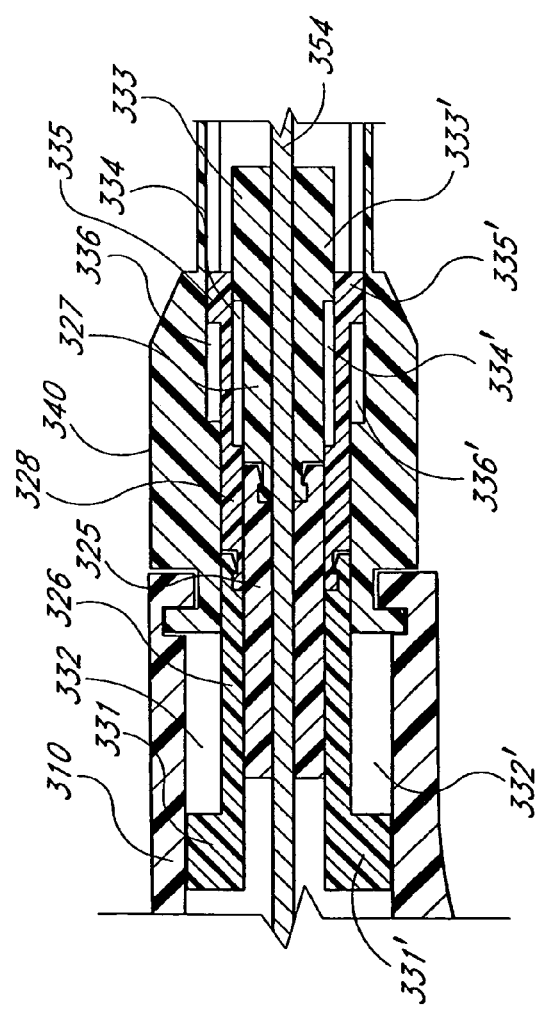
FIG. 6C is a cross-sectional side view of the cylinders and actuator rods of the preferred embodiment of a handle compatible with the present invention.
Figure 6D:
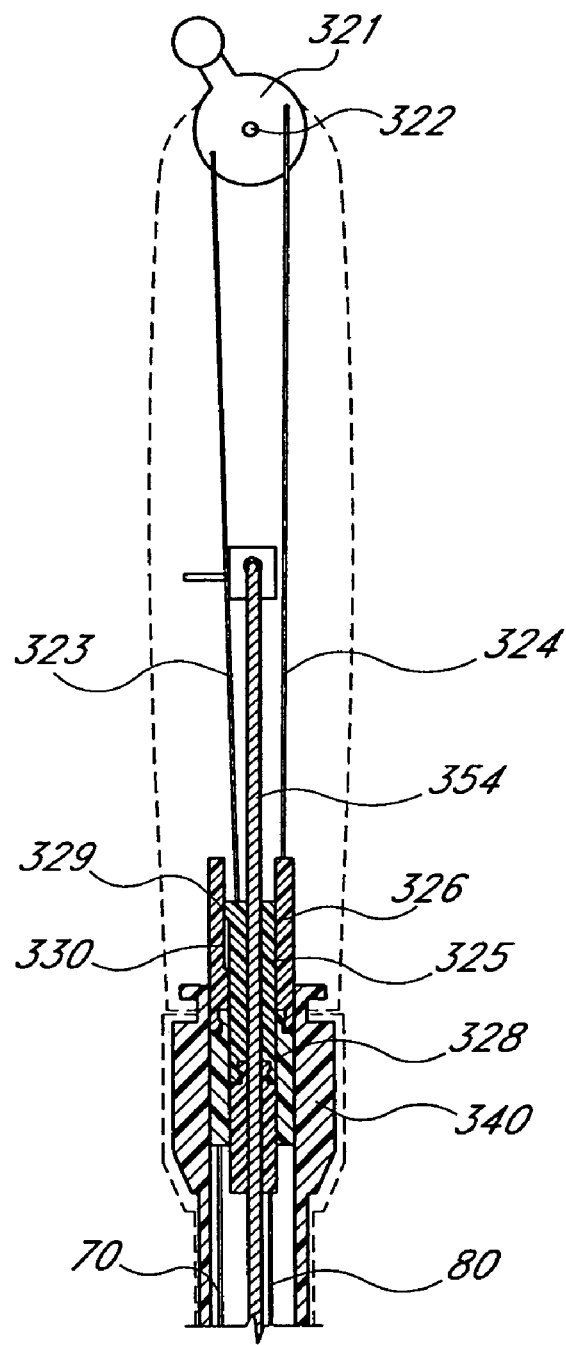
FIG. 6D is a cross-sectional top view of the preferred embodiment of a handle compatible with the present invention.

In preparation for additional suturing, the suturing mechanism assembly 12 is moved to the second orientation 210 from the first orientation 200, thereby reversing the relative positions of the first needle holder 24 and the second needle holder 34. FIG. 5E illustrates the second orientation 210 of the suturing mechanism assembly 12. In the second orientation 210, the second needle holder 34 and the needle 90 are positioned proximally to the first needle holder 24. The suturing mechanism assembly 12 can then be placed in proximity to another portion of the tissue 130 and the needle driver 110 can be extended to engage the needle 90, as illustrated in FIG. 5F. In this way, the suturing mechanism assembly 12 is then configured to begin the creation of a second stitch of the suture 100 through a second suture incision 134 in the tissue 130 in a similar manner. It will be apparent to those of skill in the art that a second suture incision 134 may be made in any suitable location relative to the first suture incision 132. After the physician has placed one or more stitches in the biological tissue 130, the physician may withdraw the suturing device 2 from the biological tissue 130. The physician may then tie a knot with the ends of the suture 100 or slide a clip down the suture 100 to tighten and secure the suture 100 on the wound.

The suturing device 2 of the preferred embodiment has particular usefulness in the field of end-to-side anastomosis, such as practiced during minimally invasive coronary artery bypass graft (CABG) procedures. In a minimally invasive CABG procedure, a series of several small ports are made in the chest wall to gain access to the thoracic cavity, typically through the third or fourth intercostal space in the midaxillary or midclavicular line. These ports provide access for various surgical tools to the area of the coronary artery bypass, such as an endoscope, irrigation and suction tools, and cutting and suturing devices. Development of devices and methods useful for assisting with such minimally invasive CABG procedures is currently an area of much activity. (See, e.g., two pending U.S. Patent applications by Nobles, U.S. patent application Ser. No. 09/121,443: "Direct Access Aortic Occlusion Device", filed Jul. 23, 1998, and U.S. patent application Ser. No. 09/193,977: "Device and Method for Partially Occluding Blood Vessels Using Flow-Through Balloon," filed Nov. 18, 1998, both of which are incorporated by reference herein.)

The CABG procedure includes end-to-side anastomosis, in which the ends of a venous or arterial graft are sutured to surgical openings made in the aortic root, and in the coronary artery at a position distal along the direction of blood flow to the coronary obstruction. The compact size and suturing method of the present invention enable successful end-to-side anastomosis in this challenging environment. During a typical procedure using the preferred embodiment of the present invention, one end of the venous graft is positioned near a corresponding opening in the aortic root. The suturing mechanism assembly 12 is then placed so that the first needle holder 24 is placed in a proximal position relative to a portion of the tissue of the one end of the graft and/or the surgical opening in the aortic root, and the second needle holder 34 is placed in a distal position relative to the same portion of tissue. A force is applied to the needle 90 by engaging the needle 90 with the needle driver 110, and extending the needle driver 110 in the distal direction. This extension of the needle driver 110 transfers the needle 90 from the first needle holder 24, through the portion of tissue between the first and second needle holders 24, 34, to the second needle holder 34. The needle driver 110 is disengaged from the needle 90 and retracted in the proximal direction away from the needle 90 and the first and second needle holders 24, 34. The first and second needle holders 24, 34 are laterally withdrawn from the portion of tissue, and the positions of the first and second needle holders 24, 34 are exchanged so that the first needle holder 24 is in a distal position relative to the second needle holder 34 and the needle 90. By placing a different portion of tissue between the first and second needle holders 24, 34, and repeating the above-described process, a series of continuous suture rows is formed thereby connecting the perimeter of the end of the venous graft to the perimeter of the opening in the aortic root. Alternatively, a series of interrupted suture rows may be formed by tying off the suture after forming each suture incision. A similar procedure is performed to connect the other end of the graft to the perimeter of a corresponding surgical opening in the coronary artery at a position distal to the obstruction along the direction of blood flow.

The handle 120 provides the physician or medical practitioner control of all the degrees of movement of the various components of the suturing device 2. FIGS. 6A-6D illustrate a preferred embodiment of the handle 120 of the present invention. The handle 120 comprises a housing 310, an arm actuator assembly 320, a rotator 340, and a needle driver actuator assembly 350. Persons skilled in the art are able to provide alternative embodiments of the handle 120 which sufficiently provide control of the various degrees of movement used to practice the present invention.

The housing 310 of the preferred embodiment of the present invention contains the various components of the handle 120 in a pistol-like configuration. Such a configuration allows the physician to operate the suturing device 2 primarily with one hand.

The arm actuator assembly 320 of the preferred embodiment of the present invention comprises a thumbwheel 321, a thumbwheel axis 322, a first linear actuator rod 323, a second linear actuator rod 324, a first inner cylinder 325, a first outer cylinder 326, a second inner cylinder 327, and a second outer cylinder 328. The thumbwheel 321 is a substantially circular disk that is rotatable about the thumbwheel axis 322 which is mounted through the center of the thumbwheel 321 and supported by recesses in the housing 310. The proximal end of the first linear actuator rod 323 is rotatably attached to the thumbwheel 321 near the perimeter of the thumbwheel 321. Similarly, the proximal end of the second linear actuator rod 324 is rotatably attached to the thumbwheel 321 near the perimeter of the thumbwheel 321 at a position 180 degrees from the attachment of the first linear actuator rod 323. The distal end of the first linear actuator rod 323 is fixedly attached to the first inner cylinder 325, and the distal end of the second linear actuator rod 323 is fixedly attached to the first outer cylinder 326.

The first inner cylinder 325 is positioned within, and coaxially to, the first outer cylinder 326. A first inner tab 329 on the first inner cylinder 325 are slidably engaged with a first outer slot 330 in the first outer cylinder 326, thereby allowing the first inner cylinder 325 to slide longitudinally without rotating in relation to the first outer cylinder 327. Similarly, a pair of first outer tabs 331, 331' on the first outer cylinder 326 are slidably engaged with a pair of first housing slots 332, 332' in the housing 310, thereby allowing the first outer cylinder 326 to slide longitudinally without rotating in relation to the housing 310.

The second inner cylinder 327 is positioned within, and coaxially to, the second outer cylinder 328. A pair of second inner tabs 333, 333' on the second inner cylinder 327 are slidably engaged with a pair of second outer slots 334, 334' in the second outer cylinder 328, thereby allowing the second inner cylinder 327 to slide longitudinally without rotating in relation to the second outer cylinder 328. Similarly, a pair of second outer tabs 335, 335' on the second outer cylinder 328 are slidably engaged with a pair of second rotator slots 336, 336' in a rotator 340, thereby allowing the second outer cylinder 328 to slide longitudinally without rotating in relation to the rotator 340. The rotator 340 is rotatably connected to the housing 310.

Both the first inner cylinder 325 and the second inner cylinder 327 have substantially the same outer diameters, and are rotatably engaged with one another in a colinear orientation. Similarly, both the first outer cylinder 326 and the second outer cylinder 328 have substantially the same outer diameters, and are rotatably engaged with one another in a colinear orientation. In addition, the proximal end of the first arm actuator rod 70 is fixedly attached to the second outer cylinder 327, and the proximal end of the second arm actuator rod 80 is fixedly attached to the second inner cylinder 328.

This configuration of coupled cylinders and actuator rods provides both the linear actuation used to operate the arms 20, 30 of the suturing mechanism assembly 12, and the rotation of the suturing mechanism assembly 12 in relation to the handle 120. By rotating the thumbwheel 321, the first linear actuator rod 323 and the second linear actuator rod 324 are longitudinally translated relative to one another. This longitudinal translation of the linear actuator rods 323, 324 results in a longitudinal translation of the inner cylinders 325, 327 relative to the outer cylinders 326, 328, and a longitudinal translation of the first arm actuator rod 70 with respect to the second arm actuator rod 80. As explained above, this motion of the arm actuator rods 70, 80 results in a transition of the suturing mechanism assembly 12 between the first orientation 200 and the second orientation 210.

Furthermore, by rotating the rotator 240 in relation to the housing 310, the second inner cylinder 327, the second outer cylinder 328, and the arm actuator rods 70, 80 are rotated in relation to the handle 120. In addition, the elongated body 10 is fixedly attached to the rotator 240, so this rotation results in a rotation of the suturing mechanism assembly 12, which can be used to orient the suturing mechanism assembly 12 to reach various portions of the tissue to be sutured.

The needle driver actuator assembly 350 comprises a trigger 351, a trigger pivot pin 352, a trigger spring 353, and a driver actuator 354. The trigger 351 is generally "racetrack"-shaped with an actuator arm 355 extending into the housing 310. The actuator arm 355 is coupled to the driver actuator 354 and to the trigger spring 353 which is attached to the actuator arm 355 and to the housing 310. The driver actuator 354 is coupled to the needle driver 110 so that a longitudinal translation of the driver actuator 354 results in a longitudinal translation of the needle driver 110, and so that the needle driver 110 maintains its orientation in relation to the rest of the suturing mechanism assembly 12 when the suturing mechanism assembly 12 is rotated with respect to the handle 120.

The trigger 351 is rotatable and pivots about the trigger pivot pin 352 which is mounted through the trigger 351 and supported by recesses in the housing 310. The driver actuator 354 slidably passes through a coaxial hole through the first inner cylinder 325 and the second inner cylinder 327. By compressing the trigger 351 against the housing 310, the actuator arm 355 pivots about the trigger pivot pin 352, thereby stretching the trigger spring 353, and extending the driver actuator 354 longitudinally in the distal direction. In this way, the physician is able to press a suture 100 through tissue 130 positioned between the first needle holder 24 and the second needle holder 34. The trigger spring 353 provides a restoring force which returns the trigger 351, driver actuator 354, and needle driver 110 to their retracted positions.

In another embodiment, illustrated in FIGS. 7A and 7B, only one needle holder 434 is used by the suturing device 402. This embodiment includes a locking pin 495 extending perpendicularly from the cylindrical proximal end 493 of the needle 490, and a needle driver 410 with a locking slot 413 and the capability of being rotated about its longitudinal axis. With the locking pin 495 engaged with the locking slot 413 of the needle driver 410, as illustrated in FIG. 7B, the needle 490 is releasably attached to the needle driver 410. Upon driving the needle 490 in the longitudinal direction through the tissue 130, the needle 490 is held by the needle holder 434 in a distal position relative to the tissue 130. The needle driver 410 is then rotated relative to the needle 490 to unlock the locking pin 495 from the locking slot 413, and the needle driver 410 is then retracted to disengage it from the needle 490. After withdrawing the suturing mechanism assembly 412 from the tissue 130, thereby pulling a sufficient length of suture 100 to provide sufficient slack, the needle driver 410 then extends and re-attaches to the needle 490 by re-engaging the locking pin 495 with the locking slot 413. The needle driver 410 then retracts from the needle holder 434, pulling the needle 490 from the needle holder 434. The suturing mechanism assembly 412 is then ready to create a second stitch of the suture 100 through another portion of tissue 130.

Alternatively, the needle 490 and the attached suture 100 are first releasably held by the needle holder 434 in a distal position relative to the tissue 130, with the needle driver 410 in a proximal position relative to the tissue 130. Upon driving the needle driver 410 in the longitudinal direction through the tissue 130, the needle driver 410 engages the needle 490 being held by the needle holder 434. The needle driver 410 is then rotated relative to the needle 490 to lock the locking pin 495 with the locking slot 413, and the needle driver 410 is then retracted to withdraw the needle in the proximal direction from the needle holder 434. In this way, the suturing mechanism assembly 412 is able to create a stitch that starts on the distal side of the tissue 130 and finishes on the proximal side of the tissue 130. The physician or medical practitioner is therefore able to choose which direction the needle 490 and suture 100 pass through the tissue 130, instead of only having the option of pushing the needle 490 in the distal direction. By pulling the suture 100 from the distal side of the tissue 130, then pushing the suture 100 from the proximal side of the tissue 130 in alternating fashion, a desirable configuration of stitches may be formed in which the suture 100 only crosses the plane of the tissue 130 by passing through the tissue 130.

Figure 8A:
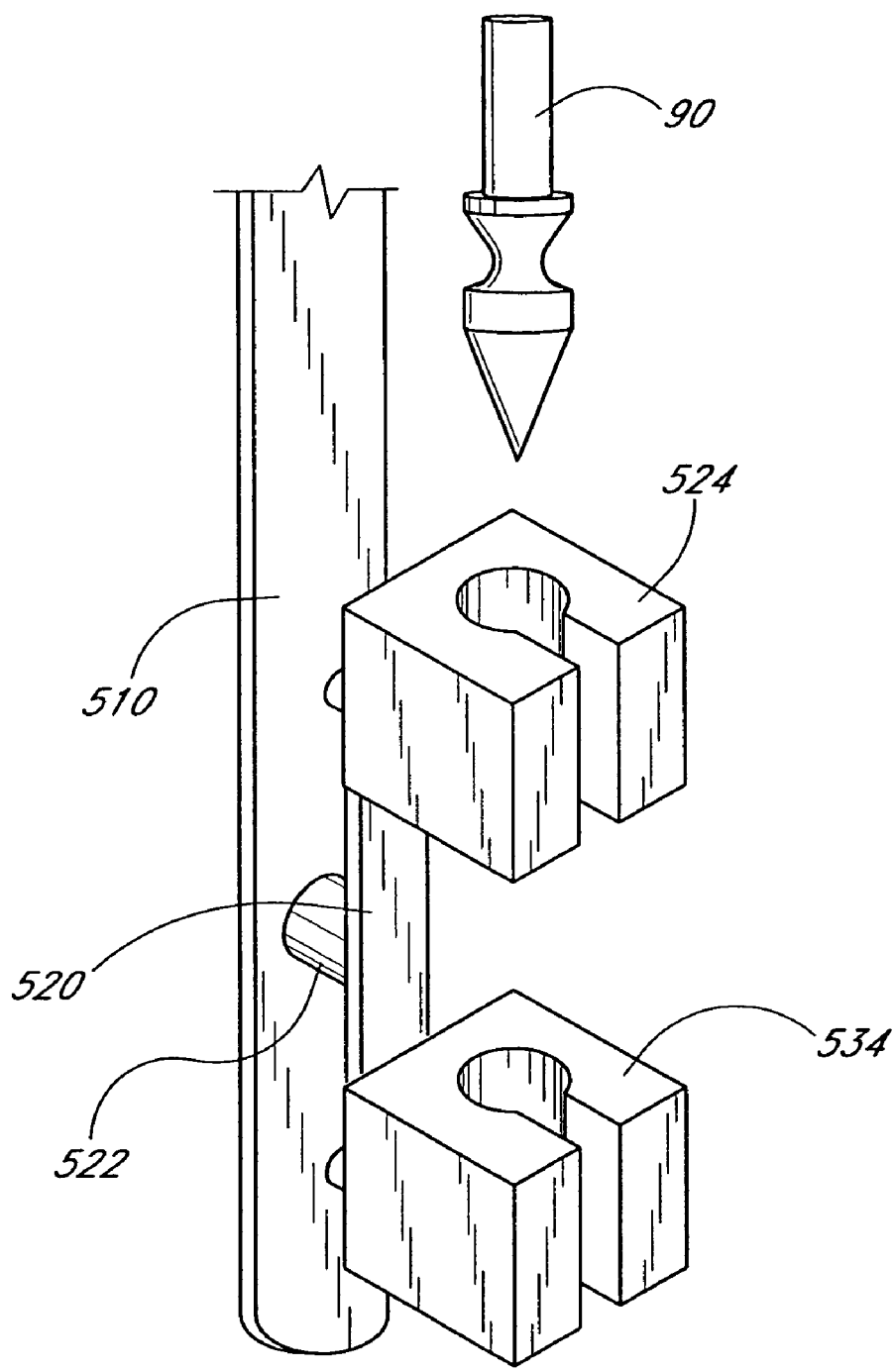
FIG. 8A is a perspective view of an alternative embodiment of the present invention comprising first and second needle holders rotatably connected to a swivel arm.
Figure 8B:
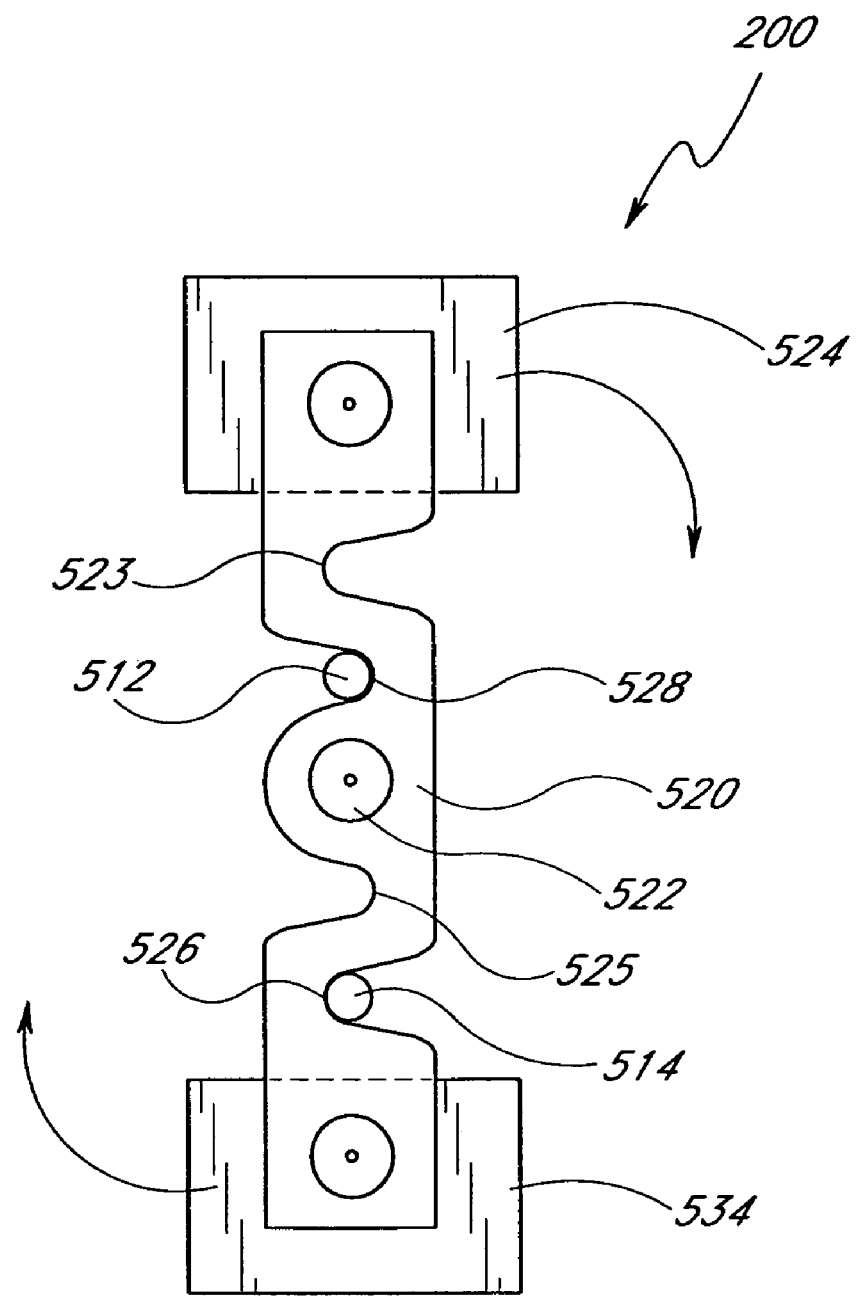
FIG. 8B is a back view of the swivel arm and locking pins of the alternative embodiment of FIG. 8A in a first orientation.
Figure 8C:
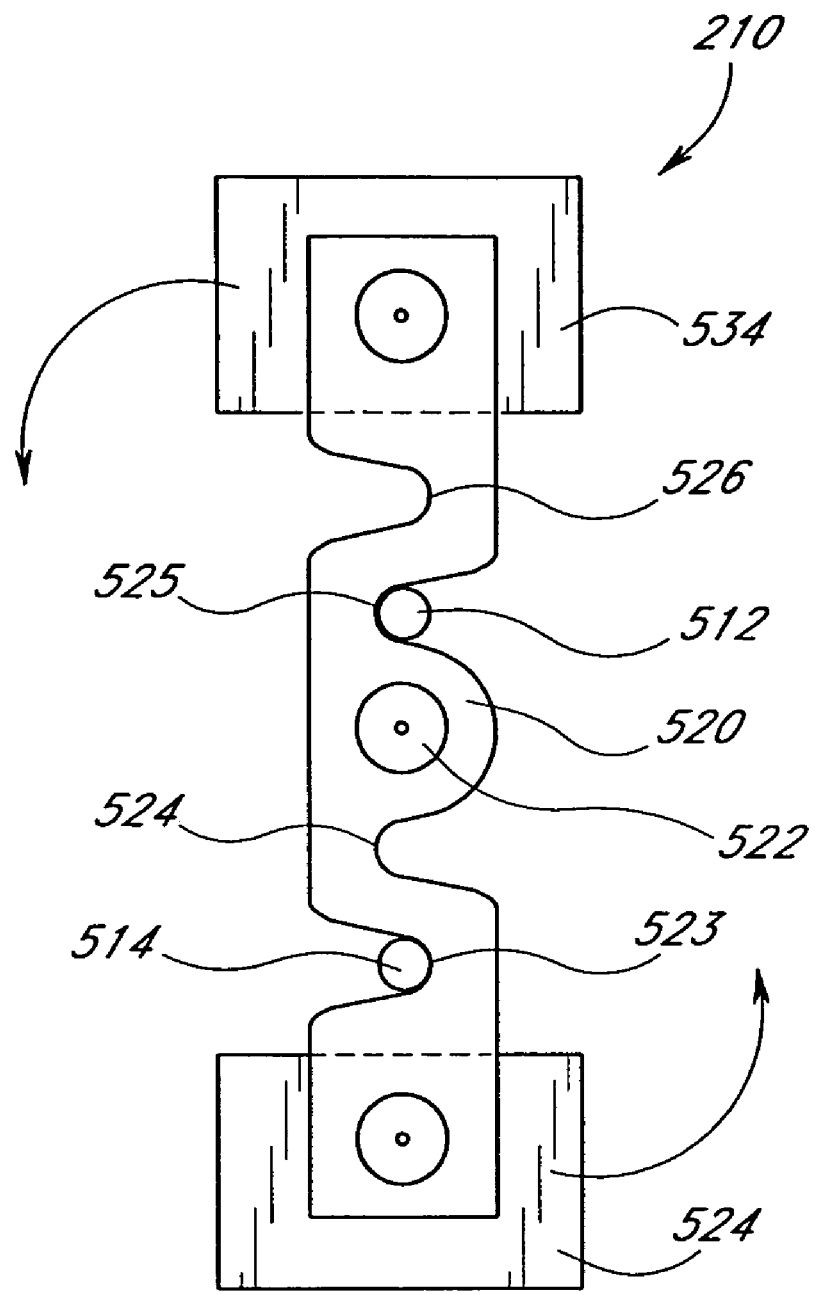
FIG. 8C is a back view of the swivel arm and locking pins of the alternative embodiment of FIG. 8A in a second orientation.

In another embodiment, illustrated in FIGS. 8A-8C, a suturing device 502 includes first and second needle holders 524, 534 rotatably connected to a swivel arm 520 which rotates in relation to the elongated body 510 about a swivel shaft 522 to alternate between the first orientation 200 and the second orientation 210. In the embodiment illustrated in FIGS. 8A-8C, the swivel shaft 522 extends from the center of the swivel arm 520, but in other embodiments, the swivel shaft 522 can be located at other positions along the swivel arm 520.

Fixedly attached to a distal portion of the elongated body 510 are a proximal locking pin 512 and a distal locking pin 514. The swivel arm 520 comprises an internal pulley system 530 and four grooves 523, 525, 526, 528 molded or otherwise shaped into a back portion of the swivel arm 520 facing the elongated body 510. The first and fourth grooves 523, 526 are configured to receive the proximal locking pin 512. The second and third grooves 528, 525 are configured to receive the distal locking pin 514. In FIG. 8B, the swivel arm 520 is in the first orientation 200 in which the proximal locking pin 512 is in the second groove 528, and the distal locking pin 514 is in the fourth groove 526. In FIG. 8C, the swivel arm 520 is in the second orientation 210, in which the proximal locking pin 512 is in the first groove 523, and the distal locking pin 514 is in the third groove 525.

The configuration of the second and fourth grooves 528, 526 and the locking pins 512, 514 prevents the swivel arm 520 from rotating counter-clockwise while the swivel arm 520 is in the first orientation 200 as illustrated in FIG. 8B. Similarly, the configuration of the first and third grooves 523, 525 and the locking pins 512, 514 prevent the swivel arm 520 from rotating clockwise while the swivel arm 520 is in the second orientation 210 as illustrated in FIG. 8C. Thus, the proximal and distal locking pins 512, 514 prevent the swivel arm 520 from rotating by more than 180 degrees in either a clockwise or a counter-clockwise direction. In alternative embodiments, other mechanisms or configurations of the suturing device 502 can be used to appropriately limit the rotation of the swivel arm 520 about the swivel shaft 522.

Alternatively, other embodiments of the suturing device 502 provide more than two positions. For example, the suturing device 502 may provide three or four positions. Likewise, other embodiments may provide rotations of less than 180 degrees or more than 180 degrees. In embodiments of the suturing device 502 with more than two positions and/or with rotations of more than or less than 180 degrees, a set of locking pins, such as the proximal and distal locking pins 512, 514 are configured to limit the movement of the swivel arm 520 accordingly. For example, one embodiment of the suturing device 502 may be configured to rotate between clockwise and/or counter-clockwise by 90 degrees by utilizing a set of locking pins to limit the rotation of the swivel arm 520 to clockwise and/or counter-clockwise by 90 degrees. Persons skilled in the art can recognize appropriate configurations of locking pins to limit the rotation of the swivel arm 520 compatible with the present invention.

The internal pulley system 530 of the swivel arm 520 comprises a series of wheels and flexible bands which have the effect of rotating the first and second needle holders 524, 534 as the swivel arm 520 is rotated about the swivel shaft 522. The internal pulley system 530 is configured to maintain the relative directional orientation of the first needle groove 526 relative to the second needle groove 536 in the first orientation 200 and second orientation 210.

Figure 9A:
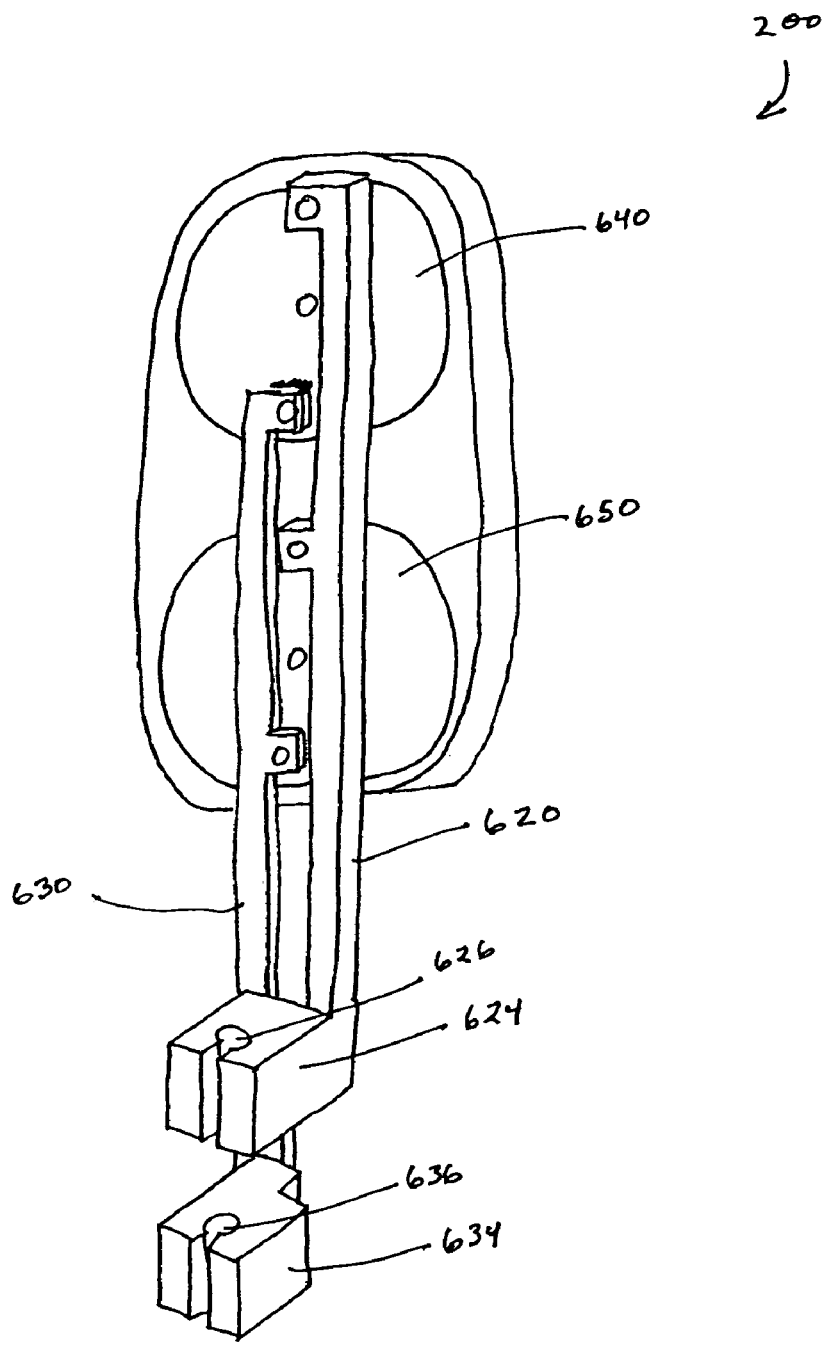
FIG. 9A is a perspective view of an alternative embodiment of the present invention comprising first and second needle holders rotatably connected to a pair of wheels.
Figure 9B:
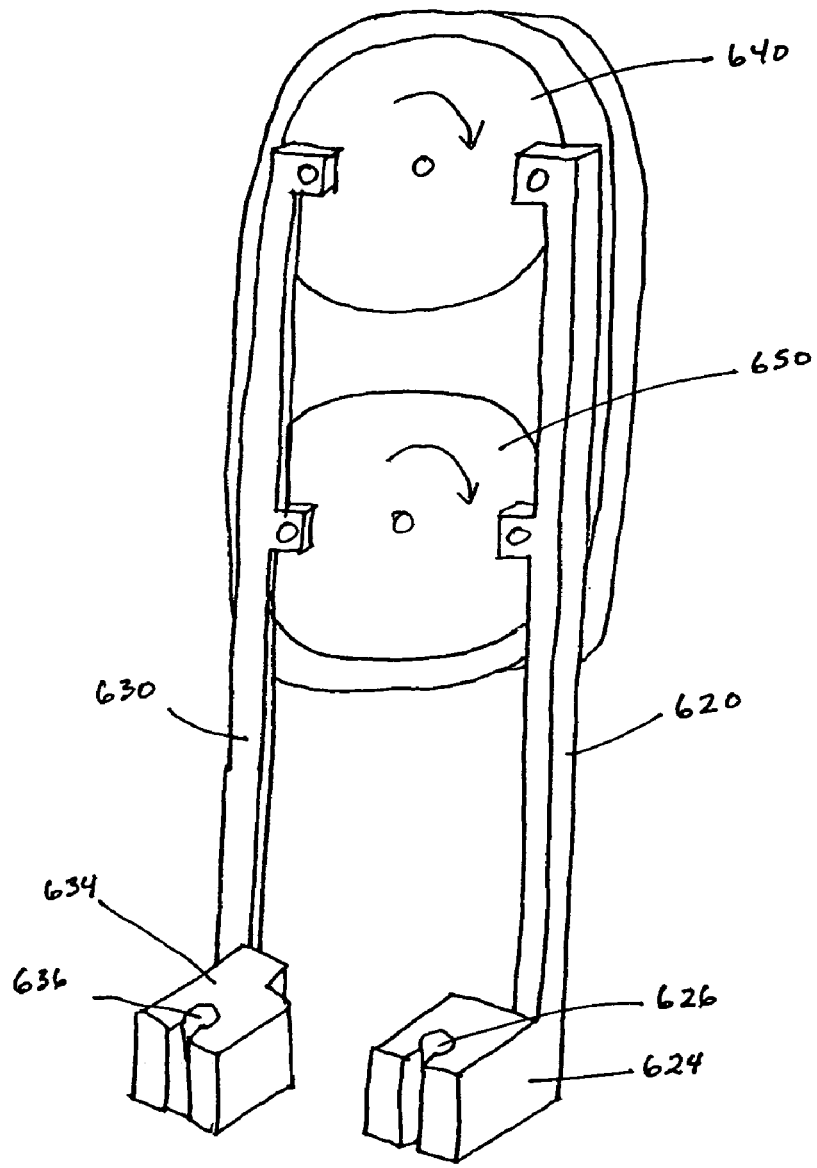
FIG. 9B is a perspective view of the alternative embodiment of FIG. 9A in an intermediate orientation between the first and second orientations.
Figure 9C:
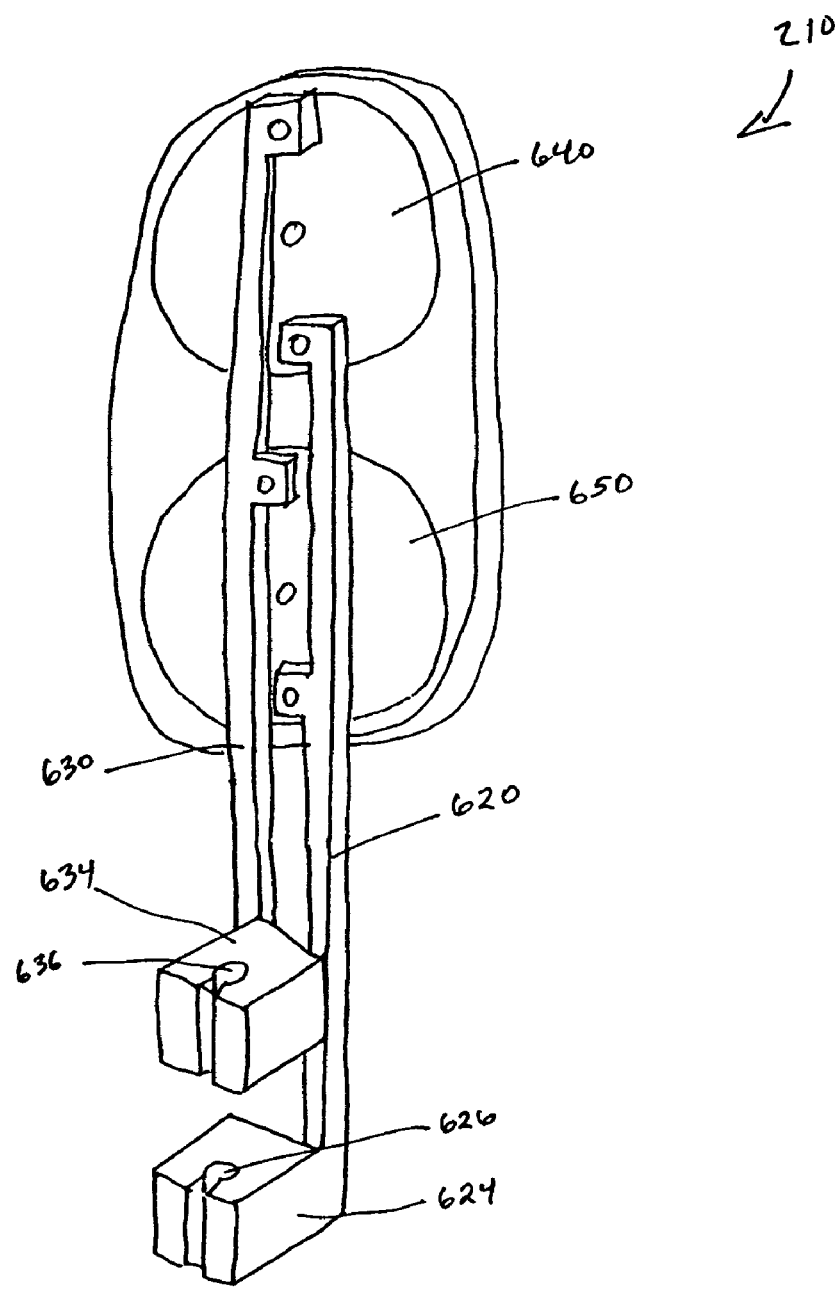
FIG. 9C is a perspective view of the alternative embodiment of FIG. 9A in the second orientation.

In another alternative embodiment of the present invention, illustrated in FIGS. 9A-9C, both a first arm 620 and second arm 630 are rotatably attached to a first wheel 640 and a second wheel 650. As illustrated in FIG. 9A, in the first orientation 200, a first needle groove 626 of a first needle holder 624 of the first arm 620 is substantially colinear with a second needle groove 636 of a second needle holder 634 of the second arm 630, with the first needle holder 624 in a proximal position relative to the second needle holder 634. To place the arms 620, 630 in the second orientation 210, the wheels 640, 650 are rotated clockwise, as illustrated in FIG. 9B. The second orientation 210 is reached once the wheels 640, 650 have rotated 180 degrees, as illustrated in FIG. 9C, thereby placing the second needle holder 634 of the second arm 630 substantially colinear with the first needle holder 624 of the first arm 620, with the second needle holder 634 in a proximal position relative to the first needle holder 624.

Figure 10A:
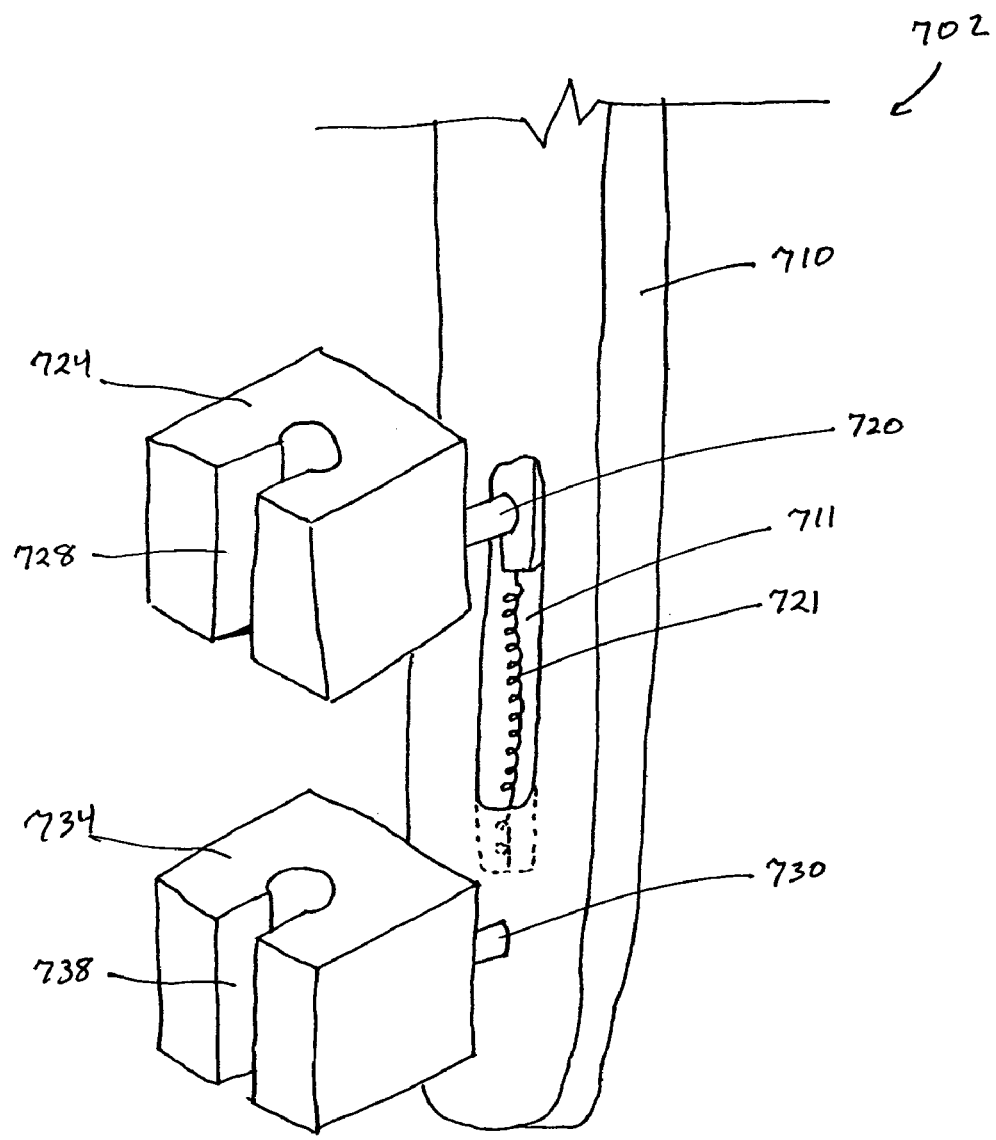
FIG. 10A is a perspective view of an alternative embodiment of the present invention comprising a first needle holder slidably attached to an elongated body.
Figure 10B:
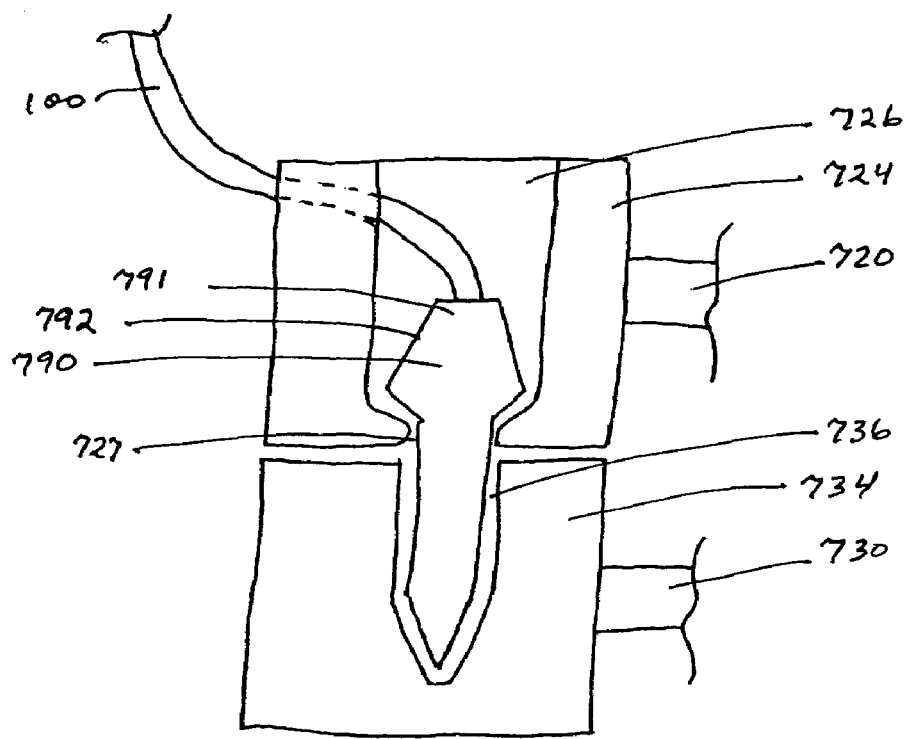
FIG. 10B is a cross-sectional view of two needle holders of the alternative embodiment of FIG. 10A with the first needle holder in its most-distal position.

In another alternative embodiment of the present invention, illustrated in FIGS. 10A and 10B, a suturing device 702 includes a first needle holder 724 which is slidably attached to an elongated body 710, via an aperture 711, a first support 720, and a biasing spring 721. A second needle holder 734 is fixedly attached to a distal portion of the elongated body 710 via a second support 730. The suture release openings 728, 738 are sufficiently wide to allow a suture 100 to slide laterally out of the needle holders 724, 734, but are sufficiently narrow to prevent the needle 790 from sliding laterally out of the needle holders 724, 734.

The first needle holder 724 is attached to the first support 720, which is partially received within the elongated body 710 through the aperture 711. The biasing spring 721 is operatively received within the elongated body 710 and provides a proximal biasing force on the first support 720. Using a linear actuator in the handle (not shown), the physician can translate the first support 720 in the distal direction, thereby bringing the first and second needle holders 724, 734 together.

FIG. 10B is a cross-sectional view of the two needle holders 724, 734 of FIG. 9A, with the first needle holder 724 in its most-distal position. In FIG. 10B, the needle 790 comprises a proximal head 791 with a sloped surface 792, which is sloped radially outward, and a locking surface 793. The proximal head 791 of the needle 790 is attached to a suture 100, and has a diameter approximately equal to or less than the diameter of a distal end 727 of the first needle groove 726. The second needle groove 736 is configured to hold the needle 790 such that the proximal head 791 of the needle 790 remains external to the second needle holder 734.

As shown in FIG. 10B, the distal portion 727 of the first needle groove 726 is sloped radially inward. The distal portion 727 of the first needle groove 726 is also made of a resilient material, which can expand from its original shape and contract back to its original shape. The distal portion 727 of the first needle groove 726 expands when the first needle holder 724 is advanced in the distal direction by the needle driver (not shown), thereby freeing the needle 790 from the first needle holder 724. The distal portion 727 of the first needle groove 726 also expands when it comes in contact with the sloped surface 792 of the proximal head 791 of the needle 790, and contracts when the proximal head 791 is completely within the first needle groove 726, thereby recapturing the needle 790 from the second needle holder 734. Once recaptured, the needle 790 is retracted from the second needle holder 734 as the first needle holder 724 is retracted in the proximal direction away from the second needle holder 734.

To use the suturing device 702 illustrated by FIGS. 10A and 10B, the physician first positions the biological tissue to be sutured (not shown) between the first and second needle holders 724, 734. The physician then actuates the needle driver to push the needle 790 in the longitudinal direction through the first needle groove 726. The distal portion 727 of the first needle groove 726 expands outward as the needle 790 is pushed distally out of the first needle groove 726. The needle driver 740 continues pushing the needle 790 longitudinally until the needle 790 pierces the biological tissue and enters the second needle groove 736 of the second needle holder 734. The needle driver 740 is then retracted in the proximal direction until it is clear of the first needle holder 724.

The physician then withdraws the suturing device 702 laterally away from the edge of the biological tissue. The physician then advances the first needle holder 724 distally until the distal portion 727 of the first needle groove 726 captures the proximal head 791 of the needle 790. The first needle holder 724 is then retracted in the proximal direction, pulling the needle 790 in the proximal direction away from the second needle holder 734. Once the first needle holder 724 is fully retracted, the physician may then position another section of biological tissue to be sutured between the needle holders 724, 734.

While embodiments and applications of this invention have been shown and described, it will be apparent to those skilled in the art that various modifications are possible without departing from the scope of the invention. It is, therefore, to be understood that within the scope of the appended claims, this invention may be practiced otherwise than as specifically described.

What is claimed is:

1. A method of suturing a portion of biological tissue using a suturing device having a longitudinal axis, a needle attached to a suture, a needle driver, and at least one needle holder, the method comprising:

(a) positioning a distal needle holder in a distal position relative to the portion of biological tissue, the distal needle holder adapted to releasably hold the needle, positioning a proximal needle holder in a proximal position relative to the portion of biological tissue, the proximal needle holder adapted to releasably hold the needle, and positioning a distal end of the needle driver in a proximal position relative to the portion of biological tissue;

(b) positioning the needle in either the proximal position or the distal position;

(c) moving the needle driver longitudinally in a first direction along a path substantially parallel to the longitudinal axis such that the needle and suture pass through the portion of biological tissue, thereby forming a suture incision through which the suture passes; and (d) repeating (a)-(c) to form a series of stitches;

wherein the needle is positioned in a proximal position relative to the portion of biological tissue by releasably holding the needle in the proximal needle holder positioned in a proximal position relative to the portion of biological tissue; and wherein the needle is positioned in the proximal position relative to the portion of biological tissue by releasably holding the needle with the distal needle holder positioned in the distal position relative to the portion of biological tissue and translating the distal needle holder to the proximal position.

2. The method of claim 1, wherein the path is straight.

3. The method of claim 1, further comprising moving the needle driver longitudinally in a second direction substantially opposite to the first direction along the path substantially parallel to the longitudinal axis.

4. The method of claim 1, wherein moving the needle driver longitudinally in the first direction advances the needle from the proximal needle holder to the distal needle holder.

5. The method of claim 4, wherein moving the needle driver longitudinally in the first direction results in the needle being releasably held by the distal needle holder.

6. The method of claim 1, wherein the distal needle holder is positioned in the distal position relative to the portion of biological tissue by placing the proximal needle holder in the distal position.

7. The method of claim 6, wherein the method further comprises releasing the needle from the needle driver after the needle is releasably held by the distal needle holder.

* * * * *

UNITED STATES PATENT AND TRADEMARK OFFICE
CERTIFICATE OF CORRECTION

PATENT NO. : 7,601,161 B1  Page 1 of 1
APPLICATION NO. : 09/607845
DATED : October 13, 2009
INVENTOR(S) : Anthony A. Nobles et al.

It is certified that error appears in the above-identified patent and that said Letters Patent is hereby corrected as shown below:

On the title page, item (75) Inventors, please change inventor's name, "Benjamin Brosh" to --Benjamin Brosch--.

At column 2, line 7, please change "resent" to --present--.

At column 10, line 4-5, please change "second outer cylinder 327," to --second outer cylinder 328,--.

At column 10, line 6, please change "second inner cylinder 328," to --second inner cylinder 327,--.

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,601,161 B1 |
| APPLICATION NO. | : 09/607845 |
| DATED | : October 13, 2009 |
| INVENTOR(S) | : Nobles et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2401 days.

Signed and Sealed this

Fifth Day of October, 2010

David J. Kappos
*Director of the United States Patent and Trademark Office*